US012128250B2

United States Patent
Wu et al.

(10) Patent No.: US 12,128,250 B2
(45) Date of Patent: Oct. 29, 2024

(54) FLUENCE MAP PREDICTION AND TREATMENT PLAN GENERATION FOR AUTOMATIC RADIATION TREATMENT PLANNING

(71) Applicant: DUKE UNIVERSITY, Durham, NC (US)

(72) Inventors: Qingrong Wu, Durham, NC (US); Yaorong Ge, Durham, NC (US); Fang-Fang Yin, Durham, NC (US); Qiuwen Wu, Durham, NC (US); Chunhao Wang, Durham, NC (US); Yang Sheng, Durham, NC (US); Xinyi Li, Durham, NC (US); Wentao Wang, Durham, NC (US)

(73) Assignees: DUKE UNIVERSITY, Durham, NC (US); THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 317 days.

(21) Appl. No.: 17/590,711

(22) Filed: Feb. 1, 2022

(65) Prior Publication Data
US 2022/0241614 A1 Aug. 4, 2022

Related U.S. Application Data

(60) Provisional application No. 63/143,985, filed on Feb. 1, 2021.

(51) Int. Cl.
*A61N 5/10* (2006.01)

(52) U.S. Cl.
CPC .................................. *A61N 5/1039* (2013.01)

(58) Field of Classification Search
CPC ......... A61N 5/10; A61N 5/103; A61N 5/1039
See application file for complete search history.

(56) References Cited

U.S. PATENT DOCUMENTS

| | | | |
|---|---|---|---|
| 8,986,186 B2 | 3/2015 | Zhang et al. | |
| 9,507,886 B2 | 11/2016 | Fiege et al. | |
| 11,065,471 B2 | 7/2021 | Wu et al. | |
| 2018/0043182 A1 | 2/2018 | Wu et al. | |
| 2019/0030370 A1 | 1/2019 | Hibbard | |
| 2020/0108276 A1 | 4/2020 | Yin et al. | |

(Continued)

OTHER PUBLICATIONS

Mahmood, Rafid et al., "Automated Treatment Planning in Radiation Therapy using Generative Adversarial Networks," Jul. 17, 2018, arXiv, 15 pages.

(Continued)

*Primary Examiner* — Jurie Yun
(74) *Attorney, Agent, or Firm* — Talem IP Law, LLP

(57) ABSTRACT

A radiation treatment planning system can include a machine learning system that receives patient data, including an image scan (e.g., CT scan) and contour(s), a physician prescription, including planning target and dose, and device (radiation beam) data and outputs predicted fluence maps. The machine learning system includes at least two stages, where a stage of the at least two stages includes converting image scans from the patient data to projection images. A treatment planning system can receive the predicted fluence maps and generates treatment plans without performing inverse optimization.

19 Claims, 12 Drawing Sheets

(56) References Cited

U.S. PATENT DOCUMENTS

2022/0088410 A1* 3/2022 Hibbard ............... G16H 20/40

OTHER PUBLICATIONS

Fan, Jiawei et al., "Automatic treatment planning based on three-dimensional dose distribution predicted from deep learning technique," Medical Physics, Jan. 2019 (accessible Nov. 1, 2018), pp. 370-381, vol. 46, issue 1.
Shaw, Edward et al., "Radiation therapy oncology group: Radiosurgery quality assurance guidelines," International Journal of Radiation Oncology*Biology*Physics, Dec. 1, 1993, pp. 1231-1239, vol. 27, issue 5.
Babier, Aaron et al., "Knowledge-based automated planning with three-dimensional generative adversarial networks," Medical Physics, Feb. 2020 (accessible Nov. 29, 2019), pp. 297-306, vol. 47, issue 2.
Wu, Qiuwen et al., "Simultaneous integrated boost intensity-modulated radiotherapy for locally advanced head-and-neck squamous cell carcinomas. I: dosimetric results," International Journal of Radiation Oncology*Biology*Physics, Jun. 2003 (accessible Jun. 1, 2003), pp. 573-585, vol. 56, issue 2.
Sheng, Yang et al., "Outlier identification in radiation therapy knowledge-based planning: A study of pelvic cases," Medical Physics, Nov. 2017, pp. 5617-5626, vol. 44, issue 11.
Mirza, Mehdi et al., "Conditional Generative Adversarial Nets," Nov. 6, 2014, arXiv, 7 pages.
Isola, Phillip et al., "Image-to-Image Translation with Conditional Adversarial Networks," Nov. 26, 2018, arXiv, 17 pages.
Piotr Porwik et al., "The Haar-Wavelet Transform in Digital Image Processing: Its Status and Achievements," Machine Graphics and Vision, Jan. 2004, pp. 79-98, vol. 13, issue 1/2.
Li, Xinyi et al., "Automatic IMRT planning via static field fluence prediction (AIP-SFFP): a deep learning algorithm for real-time prostate treatment planning," Physics in Medicine & Biology, Sep. 8, 2020 (accessible Aug. 28, 2020), 10 pages, vol. 65, issue 17, article 175014.
Wang, C. et al., "Rapid Auto IMRT Planning Using Cascade Dense Convolutional Neural Network (CDCNN): A Feasibility Study for Fluence Map Prediction Using Deep Learning on Prostate IMRT Patients," International Journal of Radiation Oncology*Biology*Physics, Sep. 2019, pp. E789-E790, vol. 105, issue 1.
He, Kaiming et al., "Deep Residual Learning for Image Recognition," Dec. 10, 2015, arXiv, 12 pages.
Huang, Gao et al., "Densely Connected Convolutional Networks," Jan. 28, 2018, arXiv, 9 pages.
Nguyen, Dan et al., "A feasibility study for predicting optimal radiation therapy dose distributions of prostate cancer patients from patient anatomy using deep learning," Scientific Reports, Jan. 31, 2019, pp. 1-10, vol. 9, issue 1, article 1076.
Zarepisheh, Masoud et al., "A DVH-guided IMRT optimization algorithm for automatic treatment planning and adaptive radiotherapy replanning," Medical Physics, May 15, 2014, pp. 1-14, vol. 41, issue 6part1, article 061711.
Sheng, Y. et al., "Outlier Identification in Radiation Therapy Knowledge Modeling: A Pelvic Planning Case Study," International Journal of Radiation Oncology*Biology*Physics, Oct. 2016, pp. E671-E672, vol. 96, issue 2S, article 3646.
Nelms, Benjamin E. et al., "Variation in external beam treatment plan quality: An inter-institutional study of planners and planning systems," Practical Radiation Oncology, Oct.-Dec. 2012, (Accessible: Jan. 9, 2012), pp. 296-305, vol. 2, issue 4.
Herman, Joseph M. et al., "Phase 2 Multi-institutional Trial Evaluating Gemcitabine and Stereotactic Body Radiotherapy for Patients With Locally Advanced Unresectable Pancreatic Adenocarcinoma," Cancer, Apr. 1, 2015, (Accessible: Dec. 23, 2014), pp. 1128-1137, vol. 121, issue 7.
Ronneberger, Olaf et al., "U-Net: Convolutional Networks for Biomedical Image Segmentation," arXiv, May 18, 2015, 8 pages.
Lee, Hoyeon et al., "Fluence-map generation for prostate intensity-modulated radiotherapy planning using a deep-neural-network," Scientific Reports, Oct. 30, 2019, pp. 1-11, vol. 9, issue 1, article 15671.
Wentao Wang et al., "Fluence Map Prediction via Deep Learning for Pancreas SBRT" (Abstract), Cureus, Apr. 2, 2020, 2 pages, vol. 12, issue 4.
Wang, Wentao et al., "Deep Learning-Based Fluence Map Prediction for Pancreas Stereotactic Body Radiation Therapy With Simultaneous Integrated Boost," Advances in Radiation Oncology, Jul. 2021 (Accessible: Feb. 15, 2021), pp. 1-9, vol. 6, issue 4, article 100672.
Koong, Albert C. et al., "Phase I study of stereotactic radiosurgery in patients with locally advanced pancreatic cancer," International Journal of Radiation Oncology*Biology*Physics, Mar. 15, 2004 (Accessible Feb. 27, 2004), pp. 1017-1021, vol. 58, issue 4.
Chuong, Michael D. et al., "Stereotactic Body Radiation Therapy for Locally Advanced and Borderline Resectable Pancreatic Cancer Is Effective and Well Tolerated," International Journal of Radiation Oncology*Biology*Physics, Jul. 1, 2013 (Accessible Apr. 5, 2013), pp. 516-522, vol. 86, issue 3.
Moningi, Shalini et al., "The Role of Stereotactic Body Radiation Therapy for Pancreatic Cancer: A Single-Institution Experience," Annals of Surgical Oncology, Jul. 2015 (accessible Jan. 7, 2015), pp. 2352-2358, vol. 22, issue 7.
Shaib, Walid L. et al., "A Phase 1 Study of Stereotactic Body Radiation Therapy Dose Escalation for Borderline Resectable Pancreatic Cancer After Modified Folfirinox (NCT01446458)," International Journal of Radiation Oncology*Biology*Physics, Oct. 1, 2016 (accessible: May 24, 2016), pp. 296-303, vol. 96, issue 2.
Petrelli, Fausto et al., "Stereotactic Body Radiation Therapy for Locally Advanced Pancreatic Cancer: A Systematic Review and Pooled Analysis of 19 Trials," International Journal of Radiation Oncology*Biology*Physics, Feb. 1, 2017 (accessible Oct. 24, 2016), pp. 313-322, vol. 97, issue 2.
Brown, Michael W. et al., "A dosimetric analysis of dose escalation using two intensity-modulated radiation therapy techniques in locally advanced pancreatic carcinoma," International Journal of Radiation Oncology*Biology*Physics, May 2006 (accessible Apr. 15, 2006), pp. 274-283, vol. 65, issue 1.
Yang, Wensha et al., "Dosimetric evaluation of simultaneous integrated boost during stereotactic body radiation therapy for pancreatic cancer," Medical Dosimetry, 2015 (accessible Oct. 22, 2014), pp. 47-52, vol. 40, issue 1.
Koay, Eugene J. et al., "Dose-Escalated Radiation Therapy for Pancreatic Cancer: A Simultaneous Integrated Boost Approach," Practical Radiation Oncology, Nov. 2020 (accessible Feb. 13, 2020), pp. e495-e507, vol. 10, issue 6.
Holmlund, Jon et al., "Adaptive Dose Escalation Trial of Stereotactic Body Radiation Therapy (SBRT) in combination with GC4419 in pancreatic cancer" (Abstract), Journal of Clinical Oncology, May 26, 2019, 2 pages, vol. 37, issue 15_suppl, article TSP4164.
Brunner, Thomas B. et al., "SBRT in pancreatic cancer: What is the therapeutic window," Radiotherapy and Oncology, Jan. 2015 (accessible Nov. 25, 2014), pp. 109-116, vol. 114, issue 1.
Yuan, Lulin et al., "Quantitative analysis of the factors which affect the interpatient organ-at-risk dose sparing variation in IMRT plans," Medical Physics, Nov. 2012 (accessible Oct. 23, 2012), pp. 6868-6878, vol. 39, issue 11.
Wu, Binbin et al., "Data-Driven Approach to Generating Achievable Dose-Volume Histogram Objectives in Intensity-Modulated Radiotherapy Planning," International Journal of Radiation Oncology*Biology*Physics, Mar. 15, 2011 (accessible Aug. 26, 2010), pp. 1241-1247, vol. 79, issue 4.
Zhu, Xiaofeng et al., "A planning quality evaluation tool for prostate adaptive IMRT based on machine learning," Medical Physics, Feb. 2011 (accessible Jan. 11, 2011), pp. 719-726, vol. 38, issue 2.
Lian, Jun et al., "Modeling the dosimetry of organ-at-risk in head and neck IMRT planning: An intertechnique and interinstitutional study," Medical Physics, Dec. 2013 (accessible Nov. 7, 2013), pp. 1-9, vol. 40, issue 12, article 121704.
Tol, Jim P. et al., "Evaluation of a Knowledge-Based Planning Solution for Head and Neck Cancer," International Journal of

(56) References Cited

OTHER PUBLICATIONS

Radiation Oncology*Biology*Physics, Mar. 1, 2015 (accessible Jan. 30, 2015), pp. 612-620, vol. 91, issue 3.
Appenzoller, Lindsey M. et al., "Predicting dose-volume histograms for organs-at-risk in IMRT planning," Medical Physics, Dec. 2012 (accessible Nov. 27, 2012), pp. 7446-7461, vol. 39, issue 12.
Skarpman Munter, Johanna et al., "Dose-volume histogram prediction using density estimation," Physics in Medicine and Biology, Sep. 7, 2015 (accessible Aug. 25, 2015), pp. 6923-6936, vol. 60, issue 17.
Schreibmann, Eduard et al., "Prior-knowledge treatment planning for volumetric arc therapy using feature-based database mining," Journal of Applied Clinical Medical Physics, Mar. 6, 2014, pp. 19-27, vol. 15, issue 2.
Shiraishi, Satomi et al., "Knowledge-based prediction of three-dimensional dose distributions for external beam radiotherapy" Medical Physics, Dec. 29, 2015, pp. 378-387, vol. 43, issue 1.
McIntosh, Chris et al., "Fully automated treatment planning for head and neck radiotherapy using a voxel-based dose prediction and dose mimicking method," Physics in Medicine & Biology, Jul. 6, 2017, pp. 5926-5944, vol. 62, issue 15.
Barragan-Montero, Ana Maria et al., "Three-dimensional dose prediction for lung IMRT patients with deep neural networks: robust learning from heterogeneous beam configurations," Medical Physics, Aug. 2019 (accessible May 18, 2019), pp. 3679-3691, vol. 46, issue 8.
Nguyen, Dan et al., "3D radiotherapy dose prediction on head and neck cancer patients with a hierarchically densely connected U-net deep learning architecture," Physics in Medicine & Biology, Mar. 18, 2019, p. 1-15, vol. 64, issue 6, article 065020.
Kearney, Vasant et al., "DoseNet: a volumetric dose prediction algorithm using 3D fully-convolutional neural networks," Physics in Medicine & Biology, Dec. 4, 2018, pp. 1-11, vol. 63, issue 23, article 235022.
Chen, Xinyuan et al., "A feasibility study on an automated method to generate patient-specific dose distributions for radiotherapy using deep learning," Medical Physics, Jan. 2019 (accessible Oct. 26, 2018), pp. 56-64, vol. 46, issue 1.
Sheng, Yang et al., "Automatic Planning of Whole Breast Radiation Therapy Using Machine Learning Models," Frontiers in Oncology, Aug. 7, 2019, pp. 1-8, vol. 9, article 750.
Cox, Brett W. et al., "Prospective Peer Review in Radiation Therapy Treatment Planning: Long-Term Results From a Longitudinal Study," Practical Radiation Oncology, Jul. 2020 (accessible Oct. 18, 2019), pp. e199-e206, vol. 10, issue 4.
Siegel, Rebecca L. et al., "Cancer statistics, 2020," CA: A Cancer Journal for Clinicians, Jan. 2020, pp. 7-30, vol. 70, issue 1.
Adelstein, David et al., "NCCN Guidelines Insights: Head and Neck Cancers, Version 2.2017," Journal of the National Comprehensive Cancer Network, Jun. 2017, pp. 761-770, vol. 15, issue 6.
Pfister, David G. et al., "NCCN Guidelines Insights: Head and Neck Cancers, Version 2.2013, Featured Updates to the NCCN Guidelines," Journal of the National Comprehensive Cancer Network, Aug. 2013, pp. 917-923, vol. 11, issue 8.
Borras, Josep M. et al., "The impact of cancer incidence and stage on optimal utilization of radiotherapy: Methodology of a population based analysis by the ESTRO-HERO project," Radiotherapy and Oncology, Jul. 2015 (accessible May 19, 2015), pp. 45-50, vol. 116, issue 1.
Quan, Enzhuo M. et al., "A Comprehensive Comparison of IMRT and VMAT Plan Quality for Prostate Cancer Treatment," International Journal of Radiation Oncology*Biology*Physics, Jul. 15, 2012, pp. 1169-1178, vol. 83, issue 4.
Amarasena, Isuru et al., "Outcomes of Routine Intensity Modulated Radiation Therapy Quality Assurance in a Large Head and Neck Cancer Center," International Journal of Radiation Oncology*Biology*Physics, Jul. 2017 (accessible Mar. 4, 2017), pp. 541-546, vol. 98, issue 3.
Hansen, Christian Rønn et al., "Automatic treatment planning improves the clinical quality of head and neck cancer treatment plans," Clinical and Translational Radiation Oncology, Dec. 2016 (accessible: Sep. 19, 2016), pp. 2-8, vol. 1.
Krayenbuehl, J. et al., "Planning comparison of five automated treatment planning solutions for locally advanced head and neck cancer," Radiation Oncology, Dec. 2018 (accessible Sep. 10, 2018), 8 pages, vol. 13, issue 170.
Tran, Bach Xuan et al., "Characterizing Artificial Intelligence Applications in Cancer Research: A Latent Dirichlet Allocation Analysis," JMIR Medical Informatics, Sep. 15, 2019 (accessible Jan. 10, 2019), pp. 1-13, vol. 7, issue 4, article e14401.
Zheng, Dandan et al., "Radiotherapy Treatment Planning in the Age of AI: Are We Ready Yet," Technology in Cancer Research Treatment, Jan. 1, 2019, 3 pages, vol. 18, article 153303381989457.
Hussein, Mohammad et al., "Automation in intensity modulated radiotherapy treatment planning—a review of recent innovations," The British Journal of Radiology, Dec. 2018 (accessible Sep. 4, 2018), 19 pages, vol. 91, issue 1092, article 20180270.
Zhang, Jiahan, et al., "Modeling of multiple planning target volumes for head and neck treatments in knowledge-based treatment planning," Medical Physics, Sep. 2019, pp. 3812-3822, vol. 46, issue 9.
Zhang, Jiahan, et al., "Knowledge-Based Tradeoff Hyperplanes for Head and Neck Treatment Planning," International Journal of Radiation Oncology*Biology*Physics, Apr. 2020 (accessible Jan. 24, 2020), pp. 1095-1103, vol. 106, issue 5.
Lahanas, Michael et al., "Multiobjective inverse planning for intensity modulated radiotherapy with constraint-free gradient-based optimization algorithms," Physics in Medicine & Biology, Sep. 7, 2003 (accessible Aug. 20, 2003), pp. 2843-2871, vol. 48, issue 17.
Monz, M. et al., "Pareto navigation-algorithmic foundation of interactive multi-criteria IMRT planning," Physics in Medicine and Biology, Feb. 21, 2008 (accessible Jan. 24, 2008), pp. 985-998, vol. 53, issue 4.
Xiao, Jianghong et al., "Multi-criteria optimization achieves superior normal tissue sparing in intensity-modulated radiation therapy for oropharyngeal cancer patients," Oral Oncology, May 2018 (accessible Apr. 4, 2018), pp. 74-81, vol. 80.
Guerrero, Mariana et al., "Multicriteria optimization: Site-specific class solutions for VMAT plans," Medical Dosimetry, 2020 (accessible May 15, 2019), pp. 7-13, vol. 45, issue 1.

\* cited by examiner

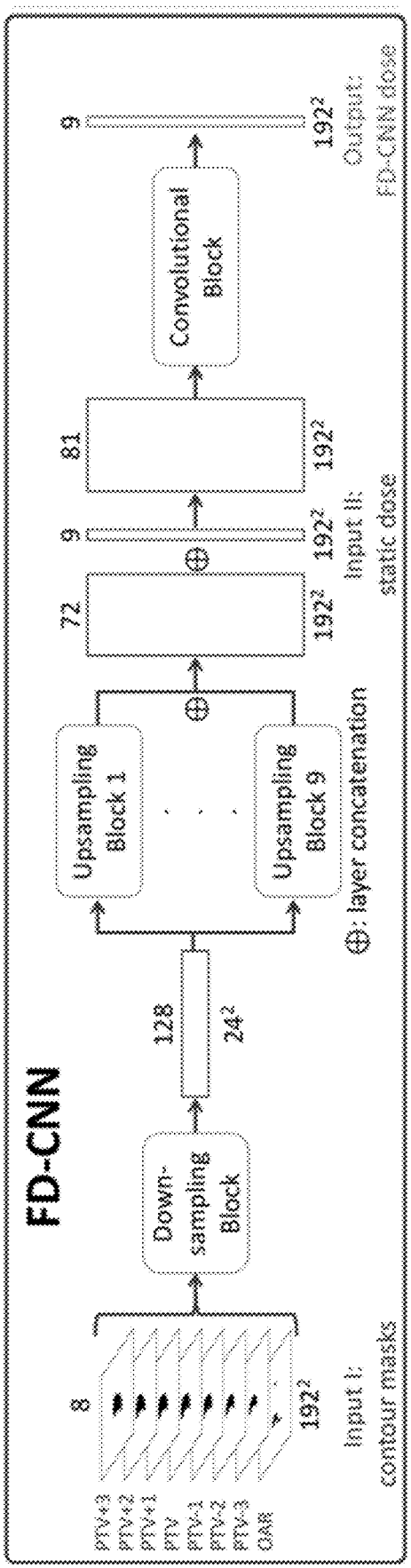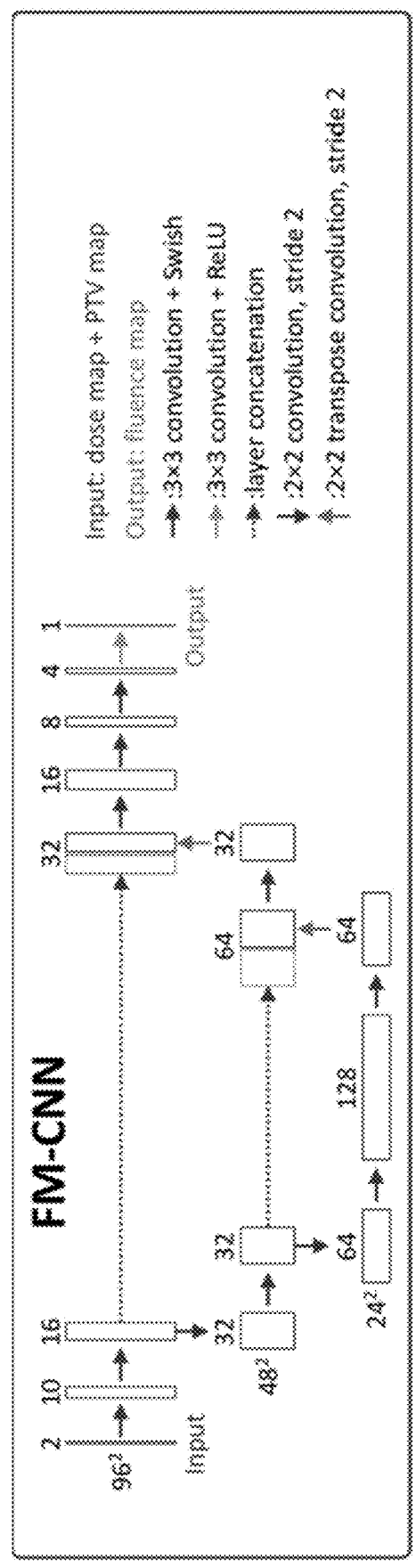
FIG. 4A
FIG. 4B

FLUENCE MAP PREDICTION AND TREATMENT PLAN GENERATION FOR AUTOMATIC RADIATION TREATMENT PLANNING

CROSS-REFERENCE TO RELATED APPLICATION

This application claims the benefit of U.S. Provisional Application Ser. No. 63/143,985, filed Feb. 1, 2021.

GOVERNMENT SUPPORT

This invention was made with Government support under Federal Grant no. R01CA201212 awarded by the National Institutes of Health. The Federal Government has certain rights to this invention.

BACKGROUND

Automatic radiation treatment planning for high-quality plans has become one of the important topics in radiation oncology. Radiation therapy, or radiotherapy, is the medical use of ionizing radiation to control malignant cells. In intensity-modulated radiation therapy (IMRT), the intensity or segment of the radiation is modified in accordance with a treatment plan to deliver highly conformal radiation doses to the planning target volume (PTV) of malignant cells, while sparing the surrounding organs at risk (OARs) and other healthy tissues from radiation damage. An IMRT treatment plan involves determining fluence maps, which indicate the number of crossing particles per defined surface area and can be used to control a dose of radiation. In conventional clinical practice, the IMRT treatment planning process is based on inverse planning. This requires an experienced human planner working in a trial-and-error fashion, as well as iterative communication between planners and other radiation oncology team members, which can be highly time-consuming.

For example, by dividing the PTV and OAR volumes into individual volume elements (or "voxels"), the IMRT treatment plan can be characterized by a three-dimensional dose distribution that characterizes the magnitude of radiation at each of the voxels (e.g., tissue sub-volumes). Another effective, two-dimensional representation of the dose distribution is the dose volume histogram (DVH). Many clinical toxicity data and guidelines relating radiation damage to organs and radiation dose are expressed in DVH parameters (i.e., x1% volume, or x2 cc volume exceeding y1% or y2 Gy of dose).

An IMRT treatment plan (or simply "IMRT plan") hereby includes all forms of treatment plans that utilize radiation treatment processes in which radiation intensity can be delivered in a non-uniform manner, including but not limited to: IMRT, volumetric modulated arc therapy (VMAT), treatment plans designed using TOMOTERPAY™, ACCURAY™, proton therapy, VIEWRAY™, VERO™, etc.

The development of an IMRT treatment plan (or simply "IMRT planning") typically involves a complex optimization procedure by which the radiation beam angles and intensities are designed to achieve required dose of radiation for the planning target volume as prescribed, as well as limit the radiation delivered to neighboring normal tissues and critical organs. Conventionally, much of the IMRT planning process requires the input and expertise of a human planner. The computerized optimization algorithm manipulates the fluence maps of radiation beams that generate the current-state dose distributions/DVHs of each PTV and OAR, and compares those values to the input dose/DVH objectives. The differences of these two sets dose/DVH values are used to adjust the strength of each radiation beamlet based on pre-determined formula and thus produce new fluence maps that improve plan quality.

One solution for IMRT planning is based on knowledge models that predict best achievable dose volume parameters or voxel dose distributions, which can reduce extra human effort and improve plan quality consistency. Recently, deep learning methods have been investigated for knowledge-based radiotherapy planning. While this has been shown to reduce planning time and improve planning consistencies, human intervention is still necessary to generate a deliverable plan, which must make the leap from desired dose parameters or dose distributions to realizable fluence maps using inverse optimization. Thus, there is an ongoing opportunity for improved automated treatment planning.

BRIEF SUMMARY

Fluence map prediction and treatment plan generation for automatic radiation treatment planning is provided.

A radiation treatment planning system can include a machine learning system that receives patient data, including an image scan (e.g., CT scan) and contour(s), a physician prescription, including planning target and dose, critical organ dose limits and priorities in meeting all the limits, and device (radiation beam) data and outputs predicted fluence maps, providing direct prediction of fluence maps (also known as radiation intensities).

The machine learning system includes at least two stages, where a stage of the at least two stages includes converting 3D images such as CT images and MRI/PET images, and associated structure contours (target, organ) from the patient data to projections along the beam direction as functional elements/parts. For example, the projections can be full or partial target projected along the beam direction, dose gradient in specific dose controlling areas projected along the beam direction, etc.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 4A and 4B show network architectures of convolutional neural networks (CNNs) for radiation treatment planning for a pancreas SBRT example.

DETAILED DESCRIPTION

Fluence map prediction and treatment plan generation for automatic radiation treatment planning is provided.

Figure 1:
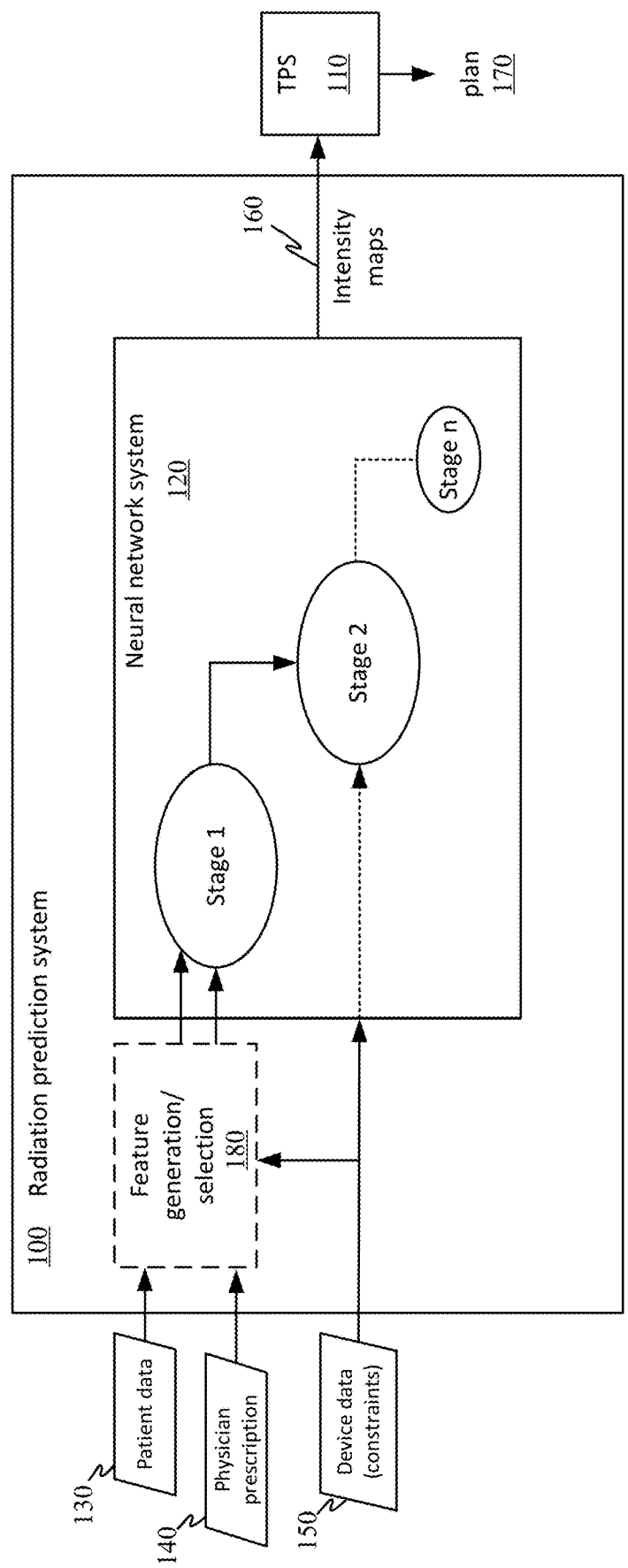
FIG. 1 illustrates a representative framework for automatic radiation treatment planning.

FIG. 1 illustrates a representative framework for automatic radiation treatment planning. Referring to FIG. 1, automatic radiation treatment planning can be accomplished using a radiation prediction system 100 and a treatment plan system (TPS) 110, which may be separate systems or part of a same computing system, for example, as described with respect to FIGS. 11A and 11B. The radiation prediction system 100 includes a machine learning system 120 that receives patient data 130, including an image scan (e.g., CT scan) and contour(s), a physician prescription 140, including planning target and dose, and device (radiation beam) data 150 and outputs fluence maps 160. The machine learning system 120 includes at least two stages, where a stage of the at least two stages includes converting image scans from the patient data to projection images. The machine learning system 120 can include one or more neural networks. In some implementations, the machine learning system 120 includes a deep neural network (DNN), a convolutional neural network (CNN) (such as U-Net), a generative adversarial network (GAN), a conditional GAN (cGAN), multiple DNNs, multiple CNNs, multiple GANs, multiple cGANs, multiple U-nets, or a combination thereof The converting of the image scans to generate projection images can involve converting 3D images such as CT images and MRI/PET images, and associated structure contours (target, organ) from the patient data to projections along the beam direction as functional elements/parts. For example, the projections can be full or partial target projected along the beam direction, dose gradient in specific dose controlling areas projected along the beam direction, etc. A method performed by the machine learning system 120 can include receiving patient data including image scans and contours; receiving prescription data including target indicating a region of interest (e.g., planning target volume); receiving device data including beam eye view information; generating projection images from the image scans in directions of potential beams to the region of interest in a patient; generating fluence maps based on the projection images; and providing the fluence maps to a treatment plan system.

The fluence maps 160 can be used by the treatment plan system 110 to generate a treatment plan 170 without using the inverse optimization process of standard TPSs. Advantageously, automatic radiation treatment planning can be accomplished based on direct prediction of fluence maps, in contrast to the previous approaches of predicting dose distributions followed by inverse optimization to generate the fluence maps.

For radiation systems using a multileaf collimator (MLC) to control the radiation beams, the treatment plan system 110 can perform leaf sequencing (e.g., for the MLC) and final dose calculation to generate a model-predicted plan 170 using the fluence maps 160.

The MLC is an intensity modulator that converts a given beam profile into a modulated profile or intensity map for the radiation treatment. An MLC is a computer-controlled collimator that has "leaves" of a high atomic numbered material that can be moved in and out of a path of a radiation beam to shape and vary the beam's intensity. For example, an MLC can have a set of leaf pairs in opposition direction with the same sizes. A leaf sequencing algorithm can be used to control the MLC to produce beam segments resulting in an appropriate fluence map for highly conformal dose coverage. Beam fluence describes the energy delivered per unit (or effective) area. In some cases, the beam output is referenced in terms of intensity, which is the energy delivered per unit area per unit time.

Feature generation/selection 180 can be provided for the machine learning system 120 that enables fewer samples to be used to model influence beam interactions. Instead of just using a selection of features directly identified from the patient data 130, specially designed features are created. In some cases, an intermediary image is created from the image scans. The intermediary image is created by generating projection images from the image scans (CT images/PET/MRI) and associated structure contours (target, organ) from the patient data in directions of potential beams to a region of interest in the patient. This enables fewer samples to be required for training the machine learning system 120.

One aspect of the present disclosure provides a method for creating radiation therapy treatment plans using direct modeling and prediction of fluence maps. In general, the method includes inputting patient anatomy and treatment prescriptions to a fluence map prediction model and creating a final treatment plan without the need for manual intervention and inverse optimization. The treatment prescriptions can include, but are not limited to, patient-specific features such as CT images and structures, as well as specially designed features based on physics principles and clinical treatment planning experience. Examples of specially designed features, which may be used for an initial stage (e.g., Stage 1) or a subsequent stage (e.g., Stage 2) of a machine learning system (e.g., machine learning system 120) may include individual beam dose and other radiation characteristics to target volume or critical organs. The specially designed features can also include physician prescriptions of target dose, organ dose tolerance, distance relationships among OARs and PTVs, and preferred tradeoff weighting among these conflicting goals.

The modeling for the machine learning system is based on patient-specific features such as anatomy, cancer targets, physician prescribed treatment goals (e.g., targeted dose, organ tolerance), clinical factors that set the preferences of the balance of the target vs. the organ, and derived features (e.g., via feature generation/selection 180) based on physics principles and clinical insights/knowledge. Once optimal fluence maps are determined, the generation of final plans is accomplished via algorithmically calculating the dose distributions. The predicted fluence maps can then optionally be imported, for example, into a commercial treatment planning system for leaf-sequencing or MLC segment generation and final dose calculation.

Due to the complex and highly nonlinear nature of the relationships between the patient features and the optimal fluence maps, advanced machine learning models, including deep learning techniques (e.g., CNN, GAN, U-net) are applied for these tasks. The disclosed method uses one or more specially designed deep learning models for determining the fluence map, as well as novel constructions of input features incorporating patient images and structures, clinical insights, treatment planning domain knowledge, and physics principles.

Figure 2:
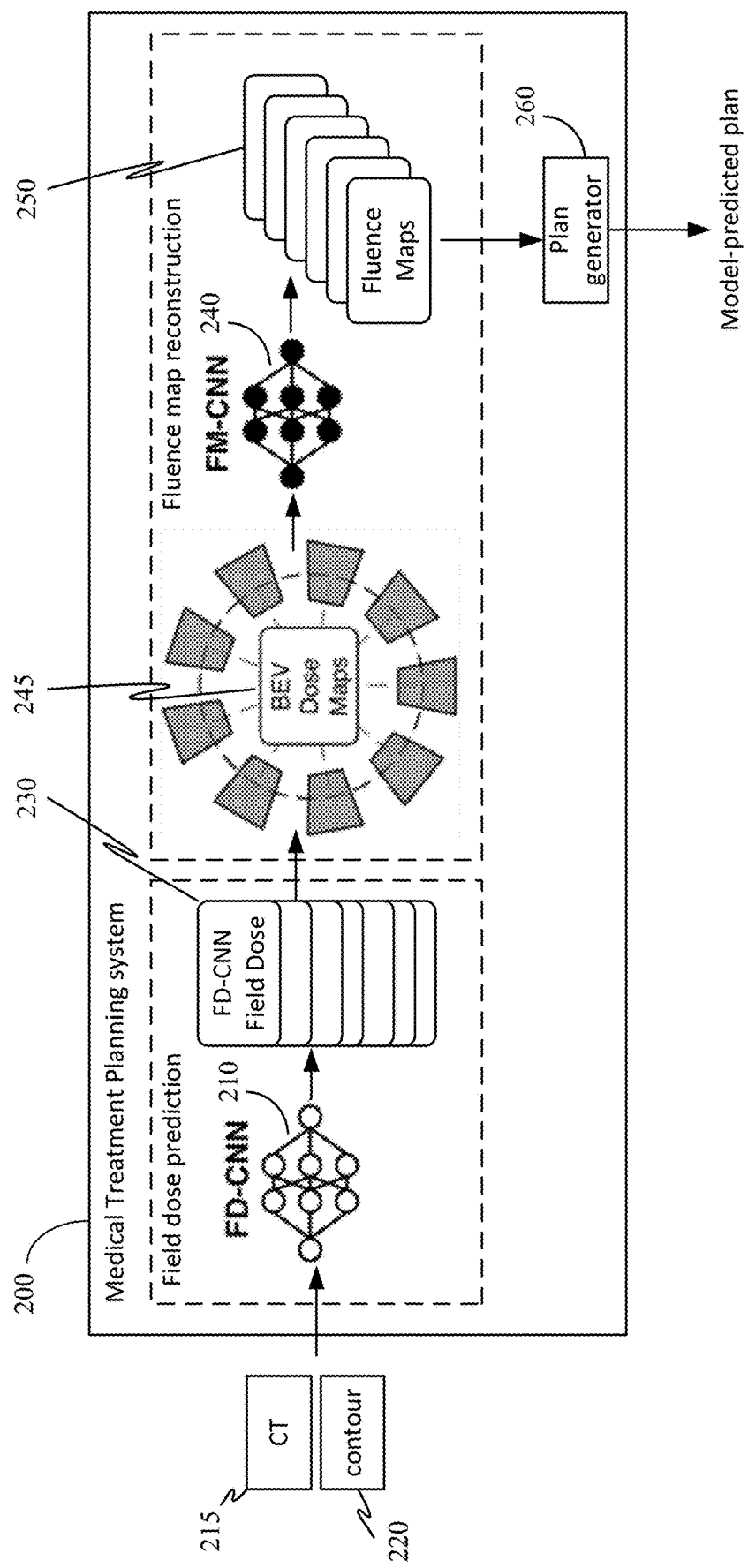
FIG. 2 shows an example implementation of an automatic radiation treatment planning system.

FIG. 2 shows an example implementation of an automatic radiation treatment planning system. Referring to FIG. 2, in accordance with the framework illustrated in FIG. 1, an automatic radiation treatment planning system 200 can perform direct plan generation using two convolutional neural networks (CNNs) (e.g., implementing machine learning system 120 of FIG. 1) to directly predict fluence maps from patient anatomy. The first CNN, field-dose CNN 210, is used for predicting field-dose distributions in a region of interest using planning images and structure contours. That is, the field-dose CNN 210 receives data including CT scans 215 with corresponding contour information 220 and outputs predicted field dose distributions 230. The second CNN, fluence map CNN 240, is used for predicting the final fluence map per beam using the predicted field dose projected onto the beam's eye view. That is, the predicted field dose distributions 230 are projected on the beam's eye view (BEV) information (e.g., in an intermediate stage), forming projected BEV dose maps 245, and the projected BEV dose maps 245 are input to the fluence map CNN 240, which outputs predicted fluence maps 250.

The predicted fluence maps 250 are then input to a plan generator 260 for generating a model-predicted plan. The field-dose CNN 210 can be considered a first stage of the machine learning system and the fluence map CNN 220 can be considered a second stage of the machine learning system. The plan generator can be embodied by a treatment plan system 110 as described with respect to FIG. 1.

As can be seen, the illustrated framework eliminates the standard IMRT inverse optimization process. The standard IMRT inverse optimization engine cycles through three components, i.e., dose/DVH evaluation, fluence maps adjustments/updates, and dose calculation using the most recent fluence maps. The desired PTV/OAR DVH values are compared against the current plan's values, and the optimization engine estimates the adjustment value for each pixel of the fluence maps. After all fluence map pixel values are adjusted, a dose calculation is performed to update the dose distribution. New DVH values are calculated from the current dose, which initiates another cycle of optimization until convergence. Finally, the TPS performs leaf sequencing or MLC segmentation and dose calculation to generate the final plan. In contrast, the system illustrated in FIG. 2 uses two sequential CNNs: one to predict dose and another to predict fluence maps, fully replacing the inverse optimization process. The predicted fluence maps are then sent to a TPS to generate the predicted plan without using the inverse optimization process of standard TPSs.

In a non-limiting example embodiment, the automatic radiation treatment planning system of FIG. 2 is used for pancreatic cancer treatment. Details of two implementations of this example embodiment are provided in Example 1 below.

Figure 3:
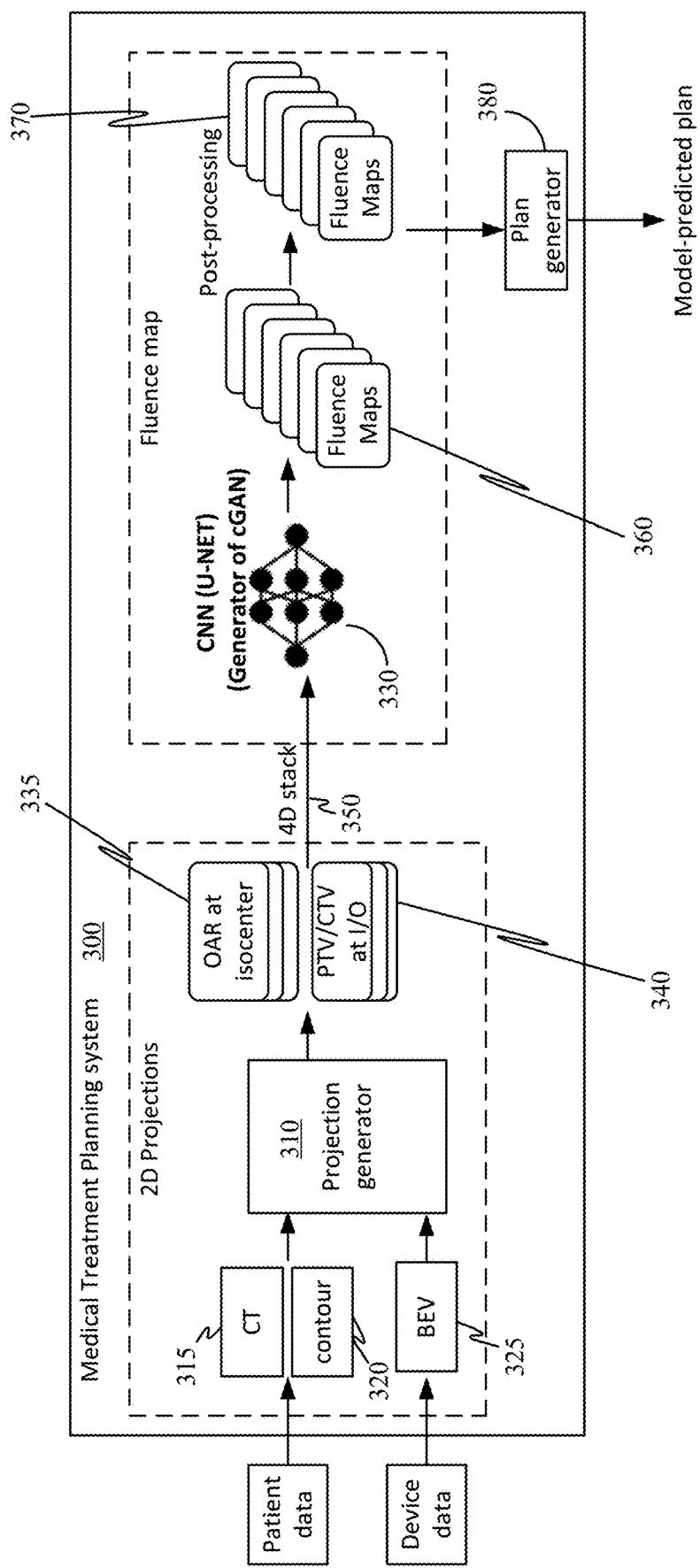
FIG. 3 shows another example implementation of an automatic radiation treatment planning system.

FIG. 3 shows an example implementation of an automatic radiation treatment planning system. Referring to FIG. 3, in accordance with the framework illustrated in FIG. 1, an automatic radiation treatment planning system 300 can perform direct plan generation. Using a two stage process, where the first stage involves a projection generator 310 that generates multiple customized 2D projections from patients' 3D CT volume 315 and structure contours 320 at each template beam angle's BEV 325 and the second stage involves a CNN 330 having a conditional Generative Adversarial Network (cGAN) architecture. The 2D projections include 1) projections 335 of each organ-at-risk (OAR) at isocenter plane; and 2) projections 340 of PTV/clinical target volume (CTV) at both entrance and exit interfaces in the BEVs. These projections are then stacked as 4D inputs 350 for the CNN 330 to generate 3D output, raw predicted fluence maps 360. The raw predicted fluence maps 360 are post-processed by Gaussian deconvolutions to provide predicted fluence maps 370, which can be used by a plan generator 380. The plan generator 380 can be embodied by a treatment plan system 110 as described with respect to FIG. 1.

In a non-limiting example embodiment, the automatic radiation treatment planning system of FIG. 3 is used for head and neck related cancer treatment. Details of this example embodiment are provided in Example 2 below with another example embodiment shown in Example 3 below.

The following Examples are provided by way of illustration and not by way of limitation. These following examples show application of the described radiation treatment planning systems and methods to prostate, pancreatic, and head and neck cancer. It should be understood that the described systems and methods are applicable to a wide range of clinical cases from the relatively simple breast and prostate to significantly more complex pancreatic and head and neck cancer types.

Example 1

Application of the described radiation treatment planning system and methods to treatment planning for pancreas stereotactic body radiation therapy (SBRT) is shown in the following example. Advantageously, by predicting fluence maps from CT and contours with field doses as intermediate products, the inverse optimization step conventionally performed for treatment planning can by bypassed.

As will be appreciated, the proposed technique can directly generate clinical-quality plans for pancreas SBRT in substantially reduced amount of time compared to conventional inverse optimization.

For this non-limiting example embodiment, a fluence map prediction model for pancreatic cancer treatment is provided. Following the example implementation of FIG. 2, the model uses two convolutional neural networks (CNNs) and comprises four basic steps. First, a Field Dose CNN (FD-CNN) predicts field dose distributions in the expanded PTV using various input features, such as computed tomography (CT) images and contours, prescription doses and organ tolerance guidance, encoded treatment planning knowledge. Second, the 3D field dose is projected to the planes that align with the fluence maps in the beam's eye view. Third, the a Fluence Map CNN (FM-CNN) predicts the final optimal fluence map per beam using the predicted field dose projections. Finally, a final plan is generated with the optimized fluence map and dose calculation.

FIGS. 4A and 4B show network architectures of the CNNs for radiation treatment planning for a pancreas SBRT example. For this example, the implementation an automatic radiation treatment planning system as shown in FIG. 2 with the CNNs implemented as shown in FIGS. 4A and 4B is used. Here, the field dose CNN (FD-CNN) predicts the field dose distributions (FD-CNN Field Dose) from CT images and contours. Then, the fluence map CNN (FM-CNN) predicts the final fluence map per beam using the previously predicted field dose's beam's eye view (BEV) projection (BEV Dose Map). Predicted fluence maps are imported into the TPS for leaf sequencing and dose calculation. For model training, benchmark plans are planned with IMRT inverse optimization by clinical physics experts. Benchmark plans' field doses and fluence maps are used as ground truths to train FD-CNN and FM-CNN.

Referring to FIG. 4A, FD-CNN (field dose CNN) predicts 9 field doses per slice and adopts a decoder-encoder structure. Among the inputs, "PTV" and "OAR" are binary contour masks of the query slice, while "PTV±n" refers to the nth PTV slice superior/inferior to the query slice; "static dose" includes TPS-calculated field doses from 9 static open beams with the same orientations as IMRT beams.

Referring to FIG. 4B, FM-CNN (fluence map CNN) predicts fluence maps from dose maps and PTV maps, which is the BEV-projected PTV binary mask. It adopts a U-net shape, including downsampling, upsampling, and skip connection. In FIGS. 4A and 4B, each rectangle represents a layer, with the number of channels on the top. Image dimensions are labeled on the bottom of each layer as shown in FIG. 4A or on the left of each hierarchy as shown in FIG. 4B.

For a first evaluation, the pancreatic cancer model described hereinabove has been realized with one hundred patients previously treated with pancreas SBRT with 85 cases randomly selected for training and 15 for testing. Nine-beam IMRT plans with a unified prescription of 33 Gy/5 fractions and organ-at-risk (OAR) (duodenum, stomach, and bowels) constraints of 25 Gy maximum (0.1 cc) were planned by a clinical physics expert and used as benchmark plans for model training and evaluation. The evaluation based on the 15 test cases showed that the average time for fluence map prediction per patient was 7.1 seconds. The PTV Dmean, Dmax, and D95% differed from benchmarks by 0.1%, 3.9%, and 2.1%, and the OAR Dmean and Dmax differed by 0.2% and 4.4%, respectively. The predicted fluence maps had comparable MUs and deliverability to the benchmark plans.

Table 1 shows a plan comparison between benchmark plans and model-predicted plans.

| Plan Type | PTV $D_{mean}$ | PTV $D_{max}$ | PTV $D_{25\%}$ | OAR $D_{mean}$ | OAR $D_{max}$ | Total MUs | Fluence Map Gamma Index |
|---|---|---|---|---|---|---|---|
| Benchmark | 103.3 ± 0.2 | 106.3 ± 0.8 | 100.3 ± 0.2 | 44.7 ± 6.2 | 71.6 ± 3.6 | 2265 ± 373 | 98.1% ± 0.7% |
| Model-predicted | 103.4 ± 1.5 | 110.4 ± 2.9 | 98.2 ± 1.4 | 44.9 ± 7.0 | 76.0 ± 6.3 | 2122 ± 281 | 97.7% ± 1.0% |

In Table 1, Dose values are reported in percentage of prescription dose. Fluence map gamma index (3 mm/3%) is calculated between optimal/predicted fluence map and actual fluence map (after leaf sequencing). All values are reported as mean±standard deviation of the 15 test cases.

Figure 5A:
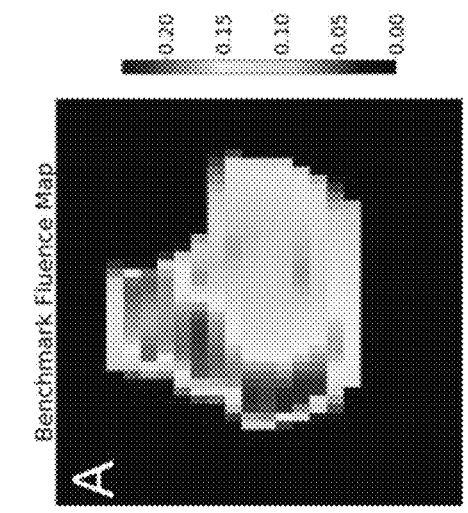
FIGS. 5A-5F show examples of fluence map prediction and dose prediction compared with a benchmark plan.
Figure 5B:
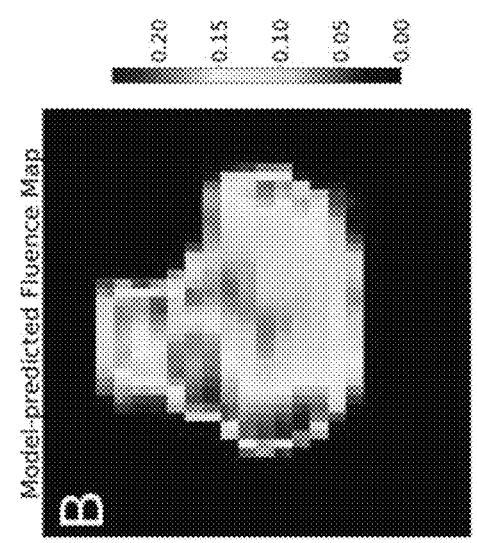
Figure 5C:
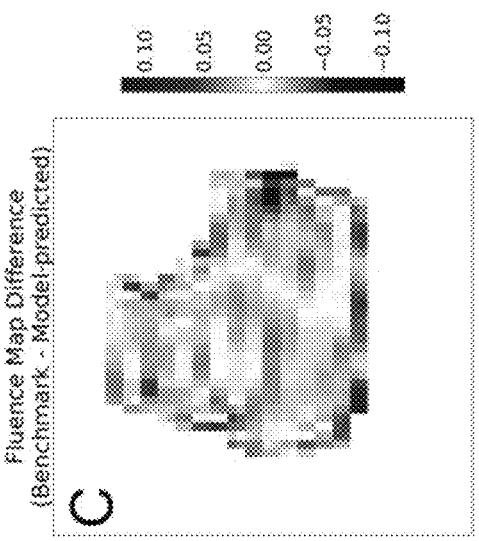
Figure 5D:
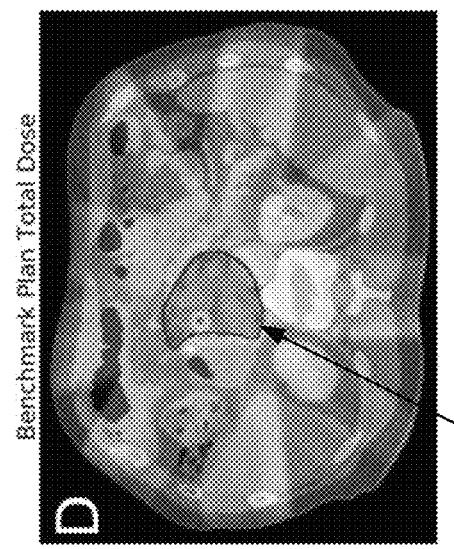
Figure 5E:
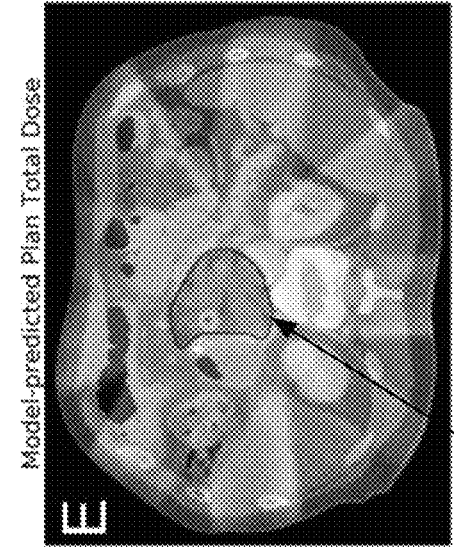
Figure 5F:
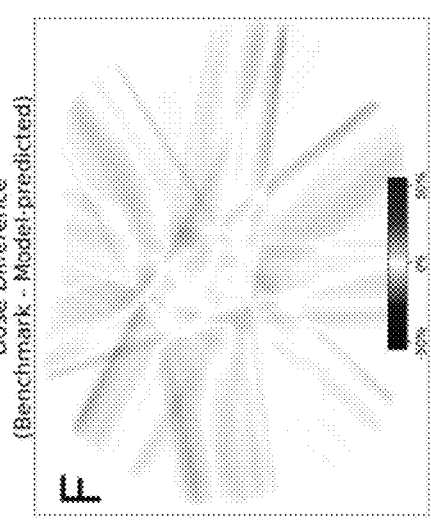

FIGS. 5A-5F show examples of fluence map prediction and dose prediction compared with a benchmark plan. FIG. 5A shows the benchmark fluence map of one beam, FIG. 5B shows the model-predicted fluence map of one beam, and FIG. 5C shows the fluence map difference (benchmark—model-predicted). Referring to FIGS. 5A-5C, it can be seen that the model-predicted fluence map recreated the fluence contrast in the benchmark. The model-predicted plan achieved similar total dose as the benchmark. FIG. 5D shows an axial slice of the total dose of the benchmark plan, FIG. 5E shows an axial slice of the total dose of the model-predicted plan, and FIG. 5F shows the dose difference (benchmark—model-predicted). The PTV is shown contoured with a line in FIGS. 5D and 5E.

Figure 6A:
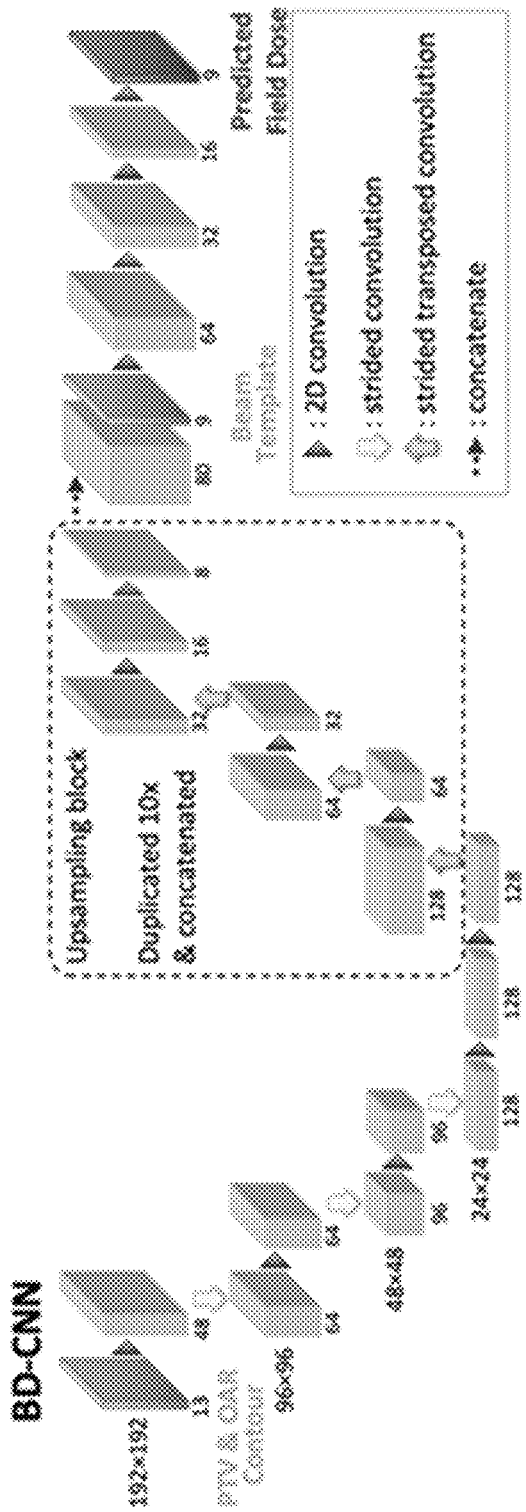
FIGS. 6A and 6B show network architectures of the CNNs for radiation treatment planning for a second pancreas SBRT example.
Figure 6B:
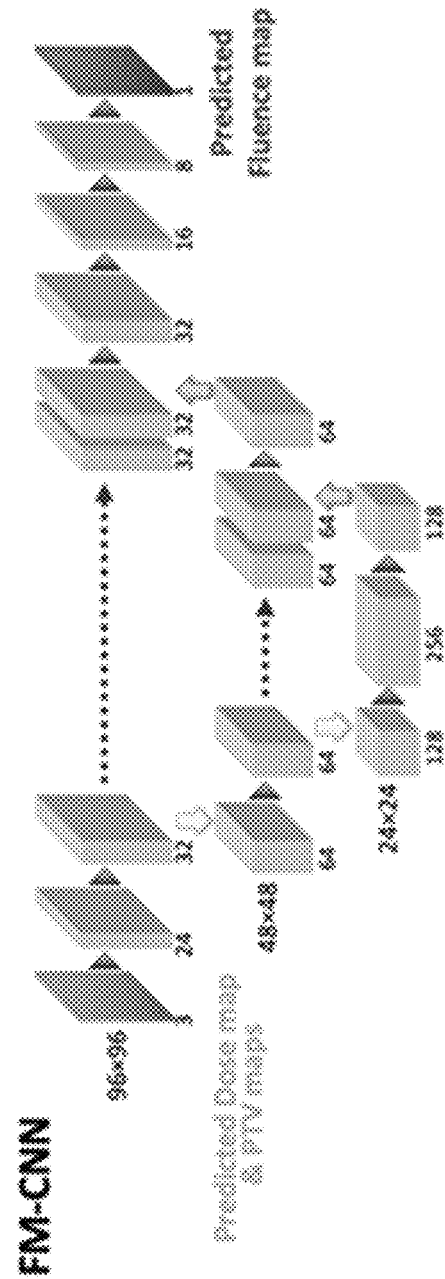

FIGS. 6A and 6B show network architectures of the CNNs for radiation treatment planning for a second pancreas SBRT example. For this example, the implementation an automatic radiation treatment planning system as shown in FIG. 2 with the CNNs implemented as shown in FIGS. 6A and 6B is used. Here, a field-dose CNN (FD-CNN) for an individual beam dose predicts the 3D dose contribution of each beam from anatomy input such as CT images and contours. Then, the fluence map CNN (FM-CNN) predicts each beam's fluence map using the previously predicted beam dose as input. Each beam's predicted dose contribution is projected along the BEV and converted to a 2D dose map. The two PTVs are converted to PTV maps as the other input. Once all nine fluence maps are predicted, they are sent to the TPS for plan finalization.

Referring to FIG. 6A, FD-CNN (field dose CNN) predicts 9 field doses per slice and adopts a decoder-encoder structure with four resolution levels. The FD-CNN in this implementation predicts nine beam doses for an axial slice with the input of PTV and OAR contours in this slice and its adjacent slices. Beam templates are stacked with feature maps after the upsampling blocks as a second input. This is repeated for every slice in a patient's region of interest. In detail, the PTV and OAR contours are converted to masks. These masks are further partitioned to reflect their dose prescriptions. For example, the PTV33 is assigned unity, and the PTV25 is assigned the relative prescription dose value (25/33). The partial volume of PTV25 overlapping with OAR is assigned the negative value of its dose limit (−29/33). The combined contour mask is fed into the network in 13 consecutive axial slices. This network extracts information from the high-resolution contour masks into low-resolution features (encoding) and reconstructs the high-resolution beam doses (decoding). Nine beam dose distributions for the central slice are generated, one in each output channel. This network design allows the independent prediction of each axial slice while incorporating contour variation in the superior-inferior direction.

Downsampling and upsampling are achieved with strided convolutional layers and strided transposed convolutional layers, respectively. The resolution of the input layer is 192×192. The downsampling block produces 128 channels with a resolution of 24×24. The upsampling block is duplicated in parallel for 10 times, each with a different set of weights and producing 8 channels with the 192×192 resolution. The outputs of the 10 upsampling blocks are stacked with the 9-channel beam templates. Finally, four convolutional layers reduce the channel number to 9, corresponding to 9 beam doses.

The loss function of the FD-CNN is defined as a weighted sum of beam dose (FD) error and total dose (TD) error, with the weight α tuned in validation. The prediction errors are calculated in a region-of-interest (ROI), which is the PTV25 expanded by 1 cm. This ROI becomes the effective whole prediction volume, since dose outside the ROI is not penalized or used in subsequent steps. The loss function is expressed as $$L_{FD} = \frac{1}{N(ROI)} \sum_{ROI} [(FD_{true} - FD_{pred})^2 + \alpha(TD_{true} - TD_{pred})^2].$$

The network was developed with Keras and Tensorflow backend. It was trained for 100 epochs. Of all the training data, 10% were held out as a validation set in order to finetune the model architecture, including the input slice numbers, the layer and channel numbers, the loss function parameters, and the use of beam templates.

Referring to FIG. 6B, the FM-CNN (fluence map CNN) takes one dose map and two PTV maps (BEV images) as the input and predicts the fluence map for one beam. It is repeated nine times for one patient.

The FM-CNN aims to reconstruct the fluence map from beam dose. The FM-CNN adopts a U-net shape with three resolution levels and predicts the fluence map for each beam individually. The input includes a dose map and the projected contour maps of PTV25 and PTV33. The dose map is each beam's predicted dose contribution (output of BD-CNN) projected along the BEV. The output is the fluence map of this beam. Both input and output have a resolution of 96×96, with a pixel size of 2.5 mm. Strided convolutional layers and strided transposed convolutional layers are used for downsampling and upsampling similar to the FD-CNN. Concatenation of layers from the left to the right side of the U-net adds skip connection to the FM-CNN.

The loss function of the FM-CNN ($L_{FM}$) is a modified mean absolute error (MAE), which is formulated as:

$$L_{FM} = (1 + \lambda) \frac{\Sigma |y_{true} - y_{pred}|}{N(y_{true} > 0)},$$

where $y_{true}$ and $y_{pred}$ are the ground truth (benchmark) and predicted values of the fluence map, and $N(y_{true}>0)$ is the count of ground truth pixels with non-zero values. $\lambda$ is a coefficient which prevents FM-CNN from over- or underestimating the fluence maps. It is expressed as $$\lambda = \frac{|N(y_{true} - y_{pred} > 0.005) - N(y_{true} - y_{pred} < -0.005)|}{N(y_{true} > 0)}.$$

For the second evaluation, one hundred pancreatic cancer patients previously treated with SBRT at Duke University Medical Center between 2014 and 2020 were randomly selected for this retrospective study under internal review board approval. 80 cases were used for training, with the remaining 20 cases for testing. Since SBRT is a rapidly evolving treatment modality for pancreatic cancer, the prescriptions to the boost target volume, the dose limits to the GI structures, as well as the treatment beam setting, have variations over time and among physicians and planners. Therefore, in this study, a set of benchmark plans were designed by clinical physicists specialized in GI treatment using the most current institutional protocol, as shown in Table 2. All benchmark plans were IMRT plans created in the Eclipse® treatment planning system (TPS, Varian Medical Systems, Palo Alto, CA) using nine equally spaced beams with angles of 20°, 60°, 100°, 140°, 180°, 220°, 260°, 300°, and 340°, which is referred to as the beam template in this study.

Table 2 shows a clinical protocol used for generating the benchmark plans

| Planning structure | Structure name | Prescription dose |
|---|---|---|
| Elective target volume | PTV25 | 25 Gy to >95% volume |
| Boost target volume | PTV33 | 33 Gy ideally to >95% volume<br>Yield to GI max dose limit |
| Duodenum<br>Stomach<br>Bowels | OAR | Maximum dose < 29 Gy |
| Bilateral kidney | Lt Kidney & Rt Kidney | $V_{15\,Gy} < 15\%$ |
| Liver | Liver | $V_{15\,Gy} < 10\%$ |

All three-dimensional plan elements, including the structures and dose distributions, were upsampled to the voxel size of 1×1×1 mm³ with linear interpolation; all the two-dimensional plan elements, including the fluence maps and other beam's eye view (BEV) projection images, maintained the original resolution of 2.5×2.5 mm².

In model training, the input and output were the projected benchmark beam dose and the benchmark fluence map from the same beam. Each patient provided 9 data samples for training. 10% of the training data were used for validation to fine tune the model architecture, including the input design, the layer and channel numbers, and the loss function parameters. The model was trained with early stopping based on validation loss.

The predicted fluence maps were imported into the TPS to create a deliverable plan via leaf sequencing (Smart LMC version 13.7.14) and dose calculation (Analytical Anisotropic Algorithm version 13.7.14). The import and calculation steps in the TPS were executed by an automated script.

The framework was evaluated in three aspects: (1) the planning time, (2) similarity of predicted fluence map and benchmark plan's fluence map, (3) dosimetry quality of the predicted plan.

To evaluate the entire framework, two CNNs were used sequentially as intended for a new patient to predict nine fluence maps directly from patient anatomy. Each step of the plan generation workflow was timed. The prediction error of each fluence map was calculated by $$Err(F_{true}, F_{pred}) = \frac{\Sigma |F_{true} - F_{pred}|}{\Sigma F_{true}}.$$

In addition to the fluence prediction error, in order to compare the similarity between the predicted fluence map and that of the benchmark plan, normalized cross correlation was calculated for each beam. A cutoff threshold of 20% was used to define the area of interest.

Although the direct outputs of the described system are fluence maps, the quality of the final plans ultimately determines the usefulness of the model in the clinic. The predicted fluence maps were imported into the Eclipse TPS to generate the predicted plan for each test case. The predicted plans were compared with the benchmark plans on clinically relevant dosimetric endpoints, including PTV33 $D_{max}$, PTV33 $D_{95\%}$, PTV33 $V_{33Gy}$, PTV33 $D_{mean}$, PTV25 $V_{25Gy}$, PTV25-33 $D_{mean}$, OAR $D_{max}$, OAR $D_{1cc}$, and OAR $D_{2cc}$. The dice coefficients between prescription (25 or 33 Gy) isodose and PTV contours were calculated to evaluate the dose conformity for both benchmark and predicted plans.

The predicted plans were evaluated and compared with the benchmark plans by a physician specialized in pancreas SBRT. With benchmark plans considered clinically acceptable, the predicted plans were assigned one of the four grades by the physician as follows: (A) comparable to benchmark, (B) slightly worse but acceptable for treatment, (C) worse and need slight modifications for treatment, (D) significantly worse and need large modifications for treatment. The performance of the plan was assigned grade point average (GPA): A for 4.0, B for 3.0, C for 2.0, and D for 1.0. The ideal GPA (4.0) is achieved by the clinical plans. It serves as a quantitative measure of clinical acceptability of the predicted plans.

In the physician's evaluation, 8 predicted plans received grade A; 5 predicted plans received grade B; 6 predicted plan received grade C; 1 predicted plan received grade D. The mean GPA of all predicted plans was 3.0. For plans with grade C or D, automated renormalization (factor within 100%±1%) was applied to satisfy PTV and OAR constraints as much as possible, which improved the grades of 6 plans from C/D to B and the overall GPA from 3.0 to 3.35, with only one plan remaining at C. The performance of the framework based on GPA showed decent plan quality. After renormalization, 19 out of 20 predicted plans were deemed acceptable by the physician to treat the patient without human intervention.

For the beam dose prediction network, FD-CNN, 7718 slices from 80 cases were used for training. The FD-CNN has 4.4 million trainable parameters, and the training process took approximately 6 hours to finish 100 epochs. Compared with the FD-CNN, the FM-CNN has fewer trainable parameters (0.8 million). There were 720 fluence maps for training the FM-CNN. The training process took 5 minutes to finish 75 epochs.

For the 20 test cases, the PTV25 volume is an excellent indicator of the input elements size (average: 234.4 cc, range: 37.1 cc-550.0 cc, standard deviation: 162.7 cc). The averaged total plan generation time is 107.2 s (range: 78.2 s-142.6 s, standard deviation: 18.3 s). Since all 3D planning elements were upsampled, data preprocessing took the longest time (average: 51.7 seconds, range: 29.6 s-94.5 s, standard deviation: 16.1 s) in the workflow. On average, individual beam's dose projection to the BEV plane took 10.8 seconds per patient (range: 3.5 s-19.5 s, standard deviation: 5.6 s), and the prediction time of the two DL models combined was only 4.73 seconds (range: 3.2 s-7.2 s, standard deviation: 1.3 s). The plan finalization step in the TPS took 40 seconds per patient, which includes leaf sequencing and final dose calculation. This step also takes place in the manual planning workflow (after inverse optimization) and lasts the same amount of time in both approaches. In total, a deliverable plan could be generated by the automated workflow within 2 minutes, which is significantly faster than manual planning.

Figure 7:
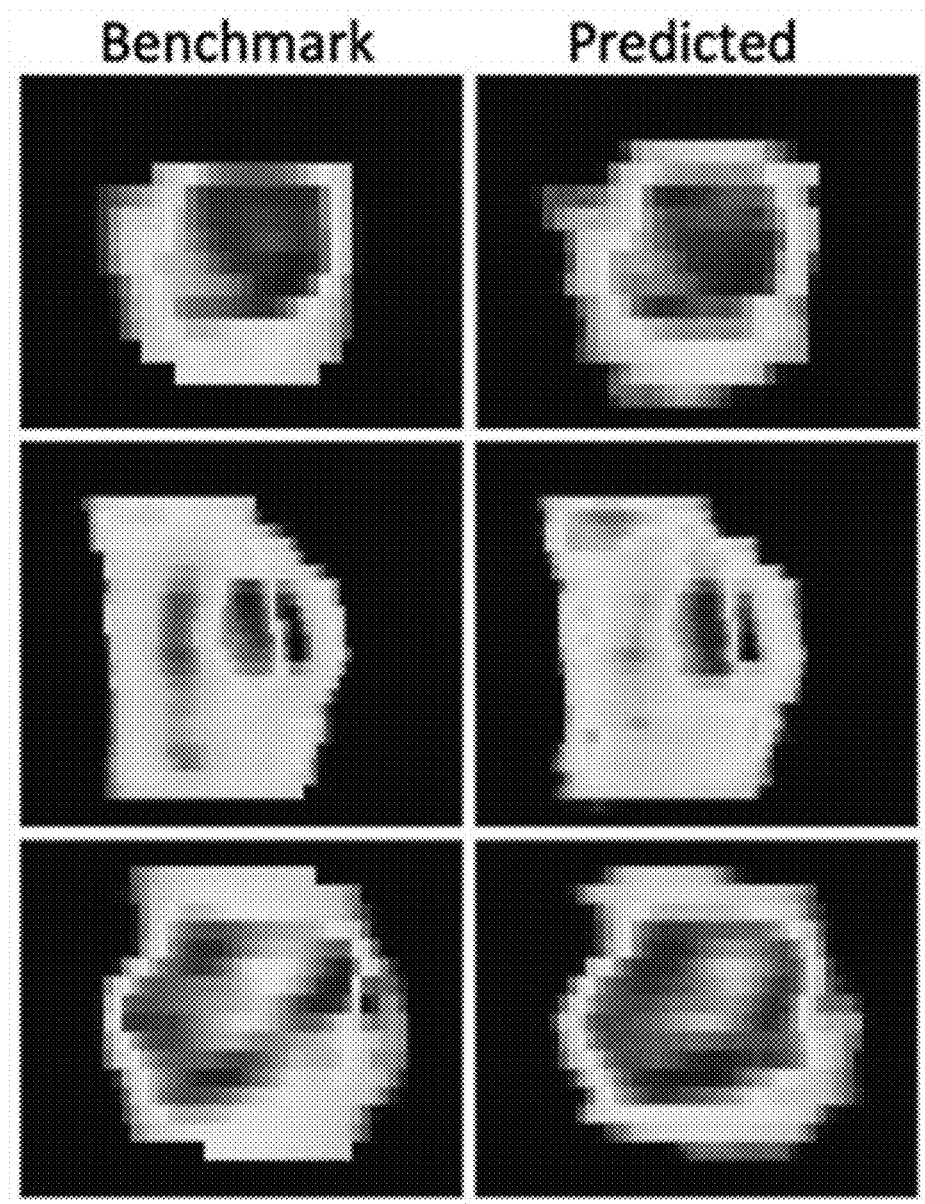
FIG. 7 shows fluence map comparisons between benchmark (left column) and predicted (right column).

The predicted fluence maps had an error (Err) of 4.0%±1.0% (mean±standard deviation) relative to the mean values of benchmark fluence maps. The normalized cross correlation between the benchmark plan's fluence map and predicted plan's fluence map was 0.949±0.022 (mean±standard deviation), with the range (0.878, 0.992). Three fluence map comparison examples are shown in FIG. 7, which are randomly selected from three different test cases. The results highlight the high similarity of the fluence map pattern between the predicted and benchmark fluence maps. FIG. 7 shows fluence map comparisons between benchmark (left column) and predicted (right column). The predicted fluence maps exhibits similar patterns as the benchmark fluence maps especially in high fluence regions, while more variations are observed in low fluence regions and near the edges.

Example 2

Application of the described radiation treatment planning system and methods to radiation treatment planning for rapid Head-and-Neck (H&N) IMRT plan generation is shown in the following example. The fluence map prediction from CT and contours can be carried out by an Artificial Intelligence (AI) agent. That is, certain aspects of the described radiation treatment planning system can be implemented as a service and, in the following example, is used to show that the proposed techniques can automatically generate IMRT plans without manual operation or inverse planning/inverse optimization. The AI agent can be utilized in the clinic for pre-planning decision-making and real-time planning.

In this non-limiting example embodiment, a fluence map prediction model for head and neck cancer treatment is provided. Following the example implementation of FIG. 3, this non-limiting example model uses a CNN (e.g., for CNN 330) that incorporates special input features derived from physics principles in addition to the patient CT images and target/organ structure features and predicts all fluence maps together using a single network. The CNN has a cGAN architecture. The generator, implemented as PyraNet, is a novel deep-learning network which implements twenty-eight classic ResNet blocks in pyramid-like concatenations. The discriminator is a customized four-layer DenseNet. A series of customized 2D projections at template beam angles are computed and stacked as 4D inputs of cGAN, from which the radiation fluence maps of each beam angle are generated simultaneously.

Figure 8:
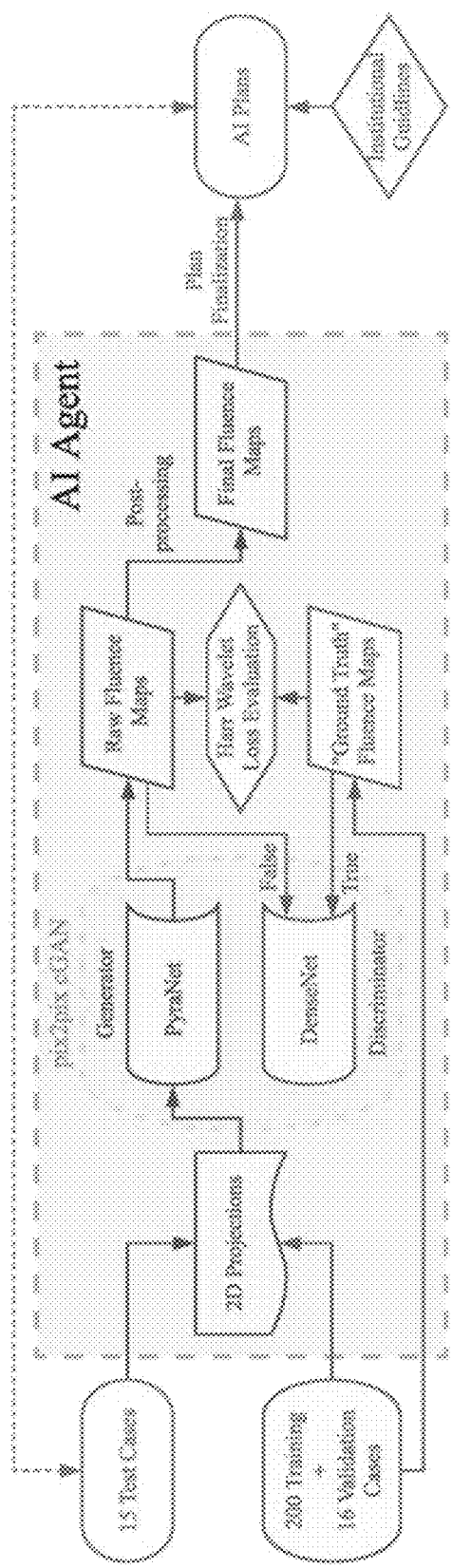
FIG. 8 shows a general workflow based on the example implementation of FIG. 3 for rapid Head-and-Neck (H&N) IMRT plan generation.

FIG. 8 shows a general workflow based on the example implementation of FIG. 3 for rapid Head-and-Neck (H&N) IMRT plan generation. Referring to FIG. 8, for a workflow for a new case, the AI agent generates 2D projections from patients' 3D CT volume and structure contours at each template beam angle's beam's eye view (BEV). These projections include 1) projections of each organ-at-risk (OAR) at isocenter plane; and 2) projections of PTV/CTV at both entrance and exit interfaces in the beams' eye views (BEVs). These projections are then stacked as 4D inputs for PyraNet to generate 3D output, raw fluence maps. The predicted fluence maps are post-processed by Gaussian deconvolutions and are sent to a commercial TPS for plan finalization, including plan integrity check and MLC leaf sequencing.

For a workflow of AI plan evaluation for independent tests, after plan finalization, AI plans are evaluated using institutional guidelines. For performance evaluation, key dosimetry metrics achieved by the AI agent were compared against the library plans during the independent tests. Isodose distribution were qualitatively assessed.

For a workflow for the AI agent's training and validation, the AI agent generates 2D projections from the training and validation cases. Similar to the new case workflow, these projections include 1) projections of each organ-at-risk (OAR) at isocenter plane; and 2) projections of PTV/CTV at both entrance and exit interfaces in the beams' eye views (BEVs). These projections are then stacked as 4D inputs for PyraNet to generate 3D output, raw fluence maps. These outputs are compared with Gaussian-smoothed ground truth radiation fluence maps through a customized Harr wavelet loss function.

Figure 9A:
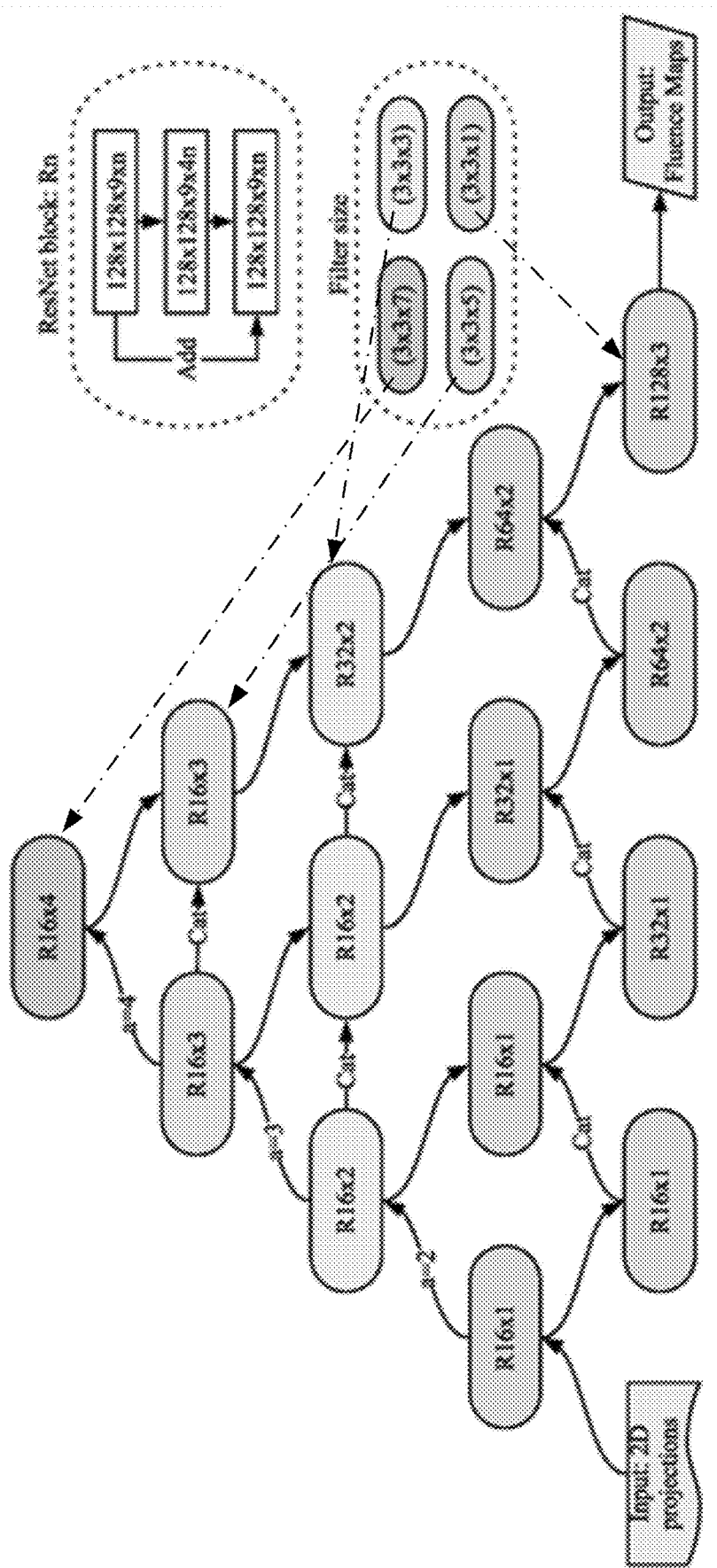
FIGS. 9A and 9B show network architecture of a conditional Generative Adversarial Network (cGAN) for the CNN of a radiation treatment planning system for a rapid Head-and-Neck (H&N) IMRT example.
Figure 9B:
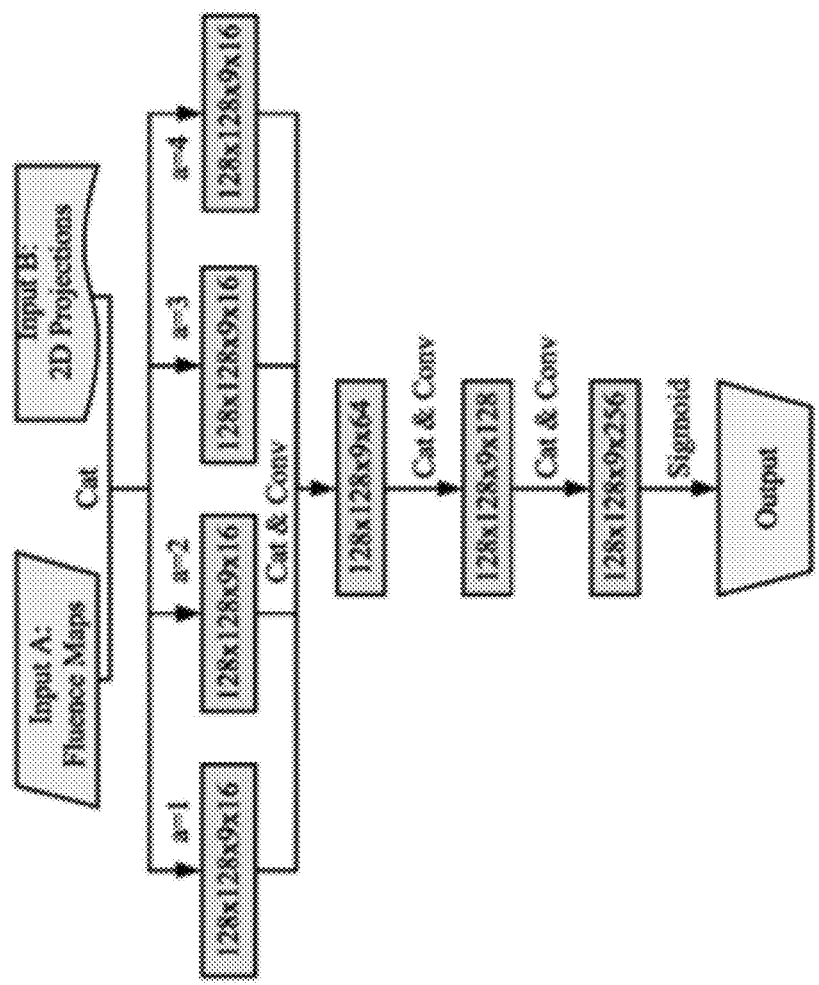

FIGS. 9A and 9B show network architecture of the cGAN for the CNN of a radiation treatment planning system for a rapid Head-and-Neck (H&N) IMRT example. As shown in FIGS. 9A and 9B, the AI agent utilizes the architecture of Pix2Pix conditional Generative Adversarial Networks (cGAN). The cGAN's generator is a novel deep learning network, PyraNet, as shown in FIG. 9A. 28 ResNet blocks were concatenated in a pyramid-like shape. The Rnxm in each node represent m cascaded ResNet block with a base feature number of n. 128×128×9×n stands for a 4D layer with n channels, where each channel contains 9 2D images (128 by 128 pixel) regarding to the 9 template beams. The nodes are color-coded with their filter sizes. When the filter size is larger than (3×3×1), the layer is cyclically padded along the dimension of beam angle before the following convolution layers in the first ResNet block in each node. All convolution layers are followed by an exponential linear unit (ELU) activation layer. The cGAN's discriminator is a customized 4-layer DenseNet, as shown in FIG. 9B. The first layer is a concatenation of 4 convolutional layers with different Atrous rates. All convolutional layers are followed by an ELU activation layer.

The head and neck cancer model described hereinabove has been built and tested with 231 oropharyngeal plans (primary plans of a sequential boost regime) where 200/16/15 plans were assigned for training/ validation/independent test, respectively. Only plans involving primary PTV were selected. To minimize plan quality variations due to fraction size variation, planning technique change, and human planner difference, all plans were replanned to form a study library. Specifically, all plans were generated by an in-house script based on Eclipse Scripting API, which has been validated for clinic use. The script started with template dose constraints and automatically adapted these constraints during inverse planning. All library cases were generated as 2 Gy/fx to 44 Gy with a fixed 9-beam field template and 6× energy on Varian TrueBeam™ machine. The template beam arrangements started at PA direction and had an increment of 40°. Shoulder avoidance of beam entrance was included.

A customized Harr wavelet loss was adopted for generator during training. In the evaluation using 15 cases, the predicted plans met all institutional planning guidelines. Isodose gradients outside of PTV were comparable. After PTV coverage normalization, Dmean of left-parotid (23.1±2.4 Gy), right-parotid (23.8±3.0 Gy) and oral cavity (24.7±6.0 Gy) were close to reference plans (23.1±2.0 Gy/23.9±2.3 Gy/23.9±4.3 Gy) without clinical differences. The predicted plans also achieved comparable results of Brainstem and cord+5 mm D 0.1 cc, but body D2cc were higher. The model took only 2 s on average for radiation fluence map prediction.

Figure 10:
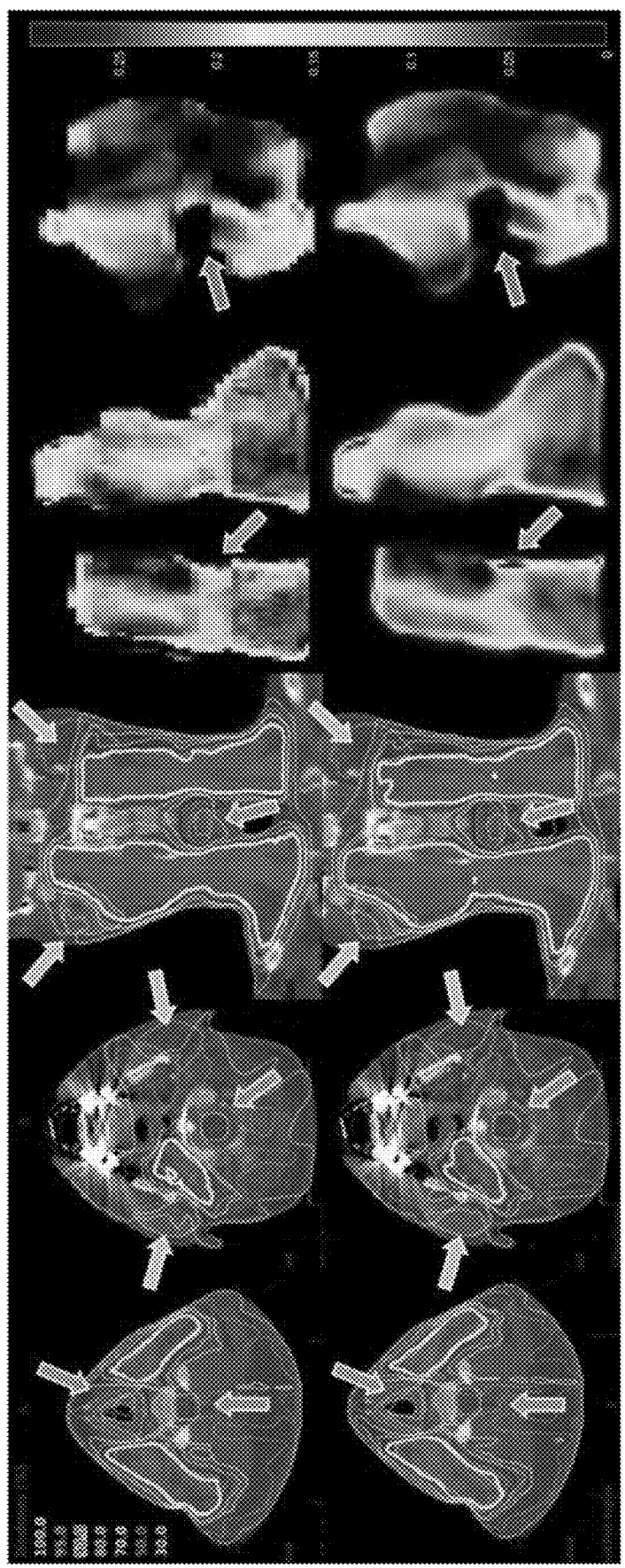
FIG. 10 shows a comparison of a library plan (upper row) and an AI plan (lower row).

FIG. 10 shows a comparison of a library plan (upper row) and an AI plan (lower row). Referring to FIG. 10, the left two columns are the transversal view of dose distribution. The right column is the frontal view of dose distribution. The fourth column is the fluence maps of beam angle 180°. The fifth column is the fluence maps of beam angle 60°. The color bar on the right is for the four fluence maps. As shown in FIG. 10, the AI plan achieved overall good isodose distribution. All OAR dosimetric parameters were comparable and acceptable for clinic use. As illustrated, cord+5 mm (orange arrows), right parotid (yellow arrows) and larynx (blue arrows) dose sparing results in the AI plan were comparable with the library plan. The fluence maps in the AI plan and the library plan also share similar features. For example, the fluence intensity on the edge is higher than inside (green arrows), and the fluence intensity is almost zero in the 60° lateral-anterior-oblique beam for larynx and pharynx avoidance (gray arrows).

Table 3 shows a dosimetric parameter evaluation between the library plans and the AI plans.

| | Library plans | AI plans |
|---|---|---|
| BODY $D_{2\,cc}$ (%) * | 109.0 ± 0.9 | 121.1 ± 3.9 |
| Brainstem $D_{0.1\,cc}$ (Gy) * | 15.0 ± 2.7 | 15.5 ± 2.1 |
| Cord + 5 mm $D_{0.1\,cc}$ (Gy) | 25.8 ± 1.9 | 27.5 ± 2.3 |
| Parotid Left $D_{mean}$ (Gy) | 23.1 ± 2.0 | 23.1 ± 2.4 |
| Parotid Left $V_{30\%}$ (%) | 64.3 ± 6.9 | 64.5 ± 9.1 |
| Parotid Right $D_{mean}$ (Gy) | 23.9 ± 2.3 | 23.8 ± 3.0 |
| Parotid Right $V_{30\%}$ (%) | 68.6 ± 11.1 | 68.7 ± 10.9 |
| Oral Cavity $D_{mean}$ (Gy) | 23.9 ± 4.3 | 24.7 ± 6.0 |
| Larynx $D_{mean}$ (Gy) * | 22.7 ± 4.8 | 21.8 ± 5.6 |
| Pharynx $D_{mean}$ (Gy) | 34.7 ± 2.5 | 35.1 ± 2.8 |

In Table 2, the "*" indicates statistical significance. All plans were normalized as PTV.

Example 3

In another example embodiment, similar to that of Example 2, a method for rapid IMRT planning of prostate SBRT is provided. This method includes an AI agent that predicts the radiation fluence maps at pre-defined static beam angles in an IMRT plan. With this AI agent, a deliverable IMRT plan can be generated in less than 20 seconds as in a real-time execution without inverse optimization. The developed AI agent centralizes a custom-designed deep-learning convolutional neural network, Dense-Res Hybrid Network (DRHN). DRHN connects four DenseNet blocks, five ResNet blocks, and one convolutional layer in a cascade architecture. The input of DRHN was 2D projections that characterize a patient's anatomy features at pre-defined beam angles, and the output of DRHN were 2D radiation fluence maps. DRHN output was sent to a commercial treatment planning system (TPS) for dose calculation and plan integrity check using a scripting interface for automated execution.

The prostate cancer model described hereinabove has been tested with 135 patients prescribed with 37 Gy in 5 fractions. 106 patients were used for the AI agent's training/validation, and the remaining 29 were used as independent tests. To minimize the plan quality dispersion, the plans for AI agent training were generated by an in-house prostate SBRT plan generator with a 7-beam arrangement and 10× flattening filter-free (FFF) energy mode. This in-house plan generator utilizes the scripting interface and automatically generate an IMRT plan based on institutional dosimetric guidelines. During the AI agent training, 2D projections with volumetric attenuation information were generated for PTV, bladder, and rectum. All projections at each beam angle were stacked as independent channels of AI agent input. The loss function was modeled as the wavelet transform errors with regions-of-interest (ROIs) weightings between the AI agent output and the ground-truth fluence maps of the training plans. 10-fold cross validation regime was employed.

The developed AI agent was evaluated in terms of plan dosimetric quality and execution efficiency. In independent test cases, key dosimetric parameters of the AI-generated plans, including 3D maximum dose and organs-at-risk (OARs) dose-volume parameters, were evaluated against institutional protocol guidelines. The investigated parameters were also compared with the corresponding values in the training plans with Wilcoxon signed-rank tests. Statistical significance level was determined at 0.05. After plan normalization (PTV D 95%=37 Gy), 28 out of 29 AI plans met all institutional dosimetric guidelines. Compared to the training plans, slightly higher max dose (~1 Gy difference) to bladder and BODY were observed in AI plans. Rectum max dose (D1cc) in AI plans were comparable with the training plans, and other rectum dosimetric results (D75%, D60%, D50%) were slightly improved from the training plans without significance. Each AI plan was generated in less than 20 seconds in a fully automated execution.

System Configurations

Figure 11A:
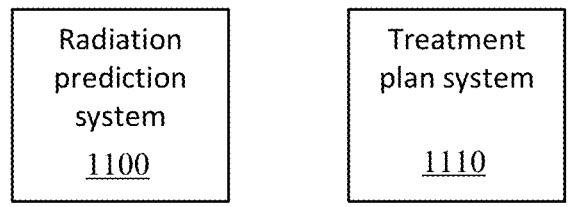
FIGS. 11A and 11B illustrate example configurations of an automatic radiation treatment planning system.
Figure 11B:
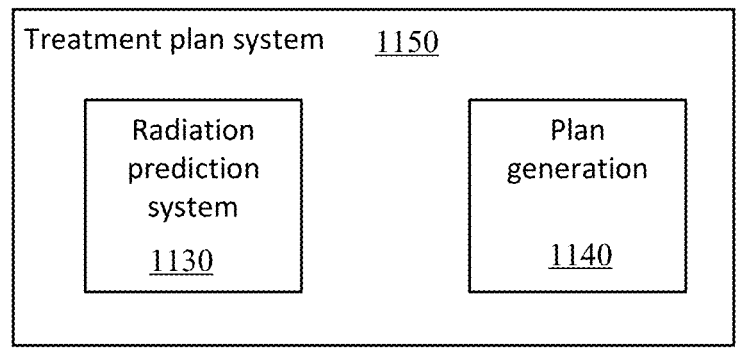

FIGS. 11A and 11B illustrate example configurations of an automatic radiation treatment planning system. Referring to FIG. 11A, the radiation prediction system 1100 (such as that described with respect to FIG. 1) can be a separate system from the treatment plan system 1110, where each may be implemented as described with respect to computing system 1200 of FIG. 12. Referring to FIG. 11B, the radiation prediction system 1130 (such as described with respect to FIG. 1) can be part of a same system as the plan generation system 1140 (and may be considered together as a treatment plan system 1150). The treatment plan system 1150 can be implemented as described with respect to computing system 1200 of FIG. 12.

Another aspect of the present disclosure provides a system for predicting fluence maps. The system comprises a computing system configured to execute the methods described hereinabove, and it optionally comprises a radiation treatment system that is in electronic communication with the computing system. In some embodiments, the system can generate IMRT/VMAT plans with the predictive model involving one or more deep learning neural networks.

In some embodiments, fluence maps can be achieved by predicting MLC segments or other mechanisms that determine fluence maps. Additionally, the deep learning neural networks can have variations of convolution neural network architectures.

Figure 12:
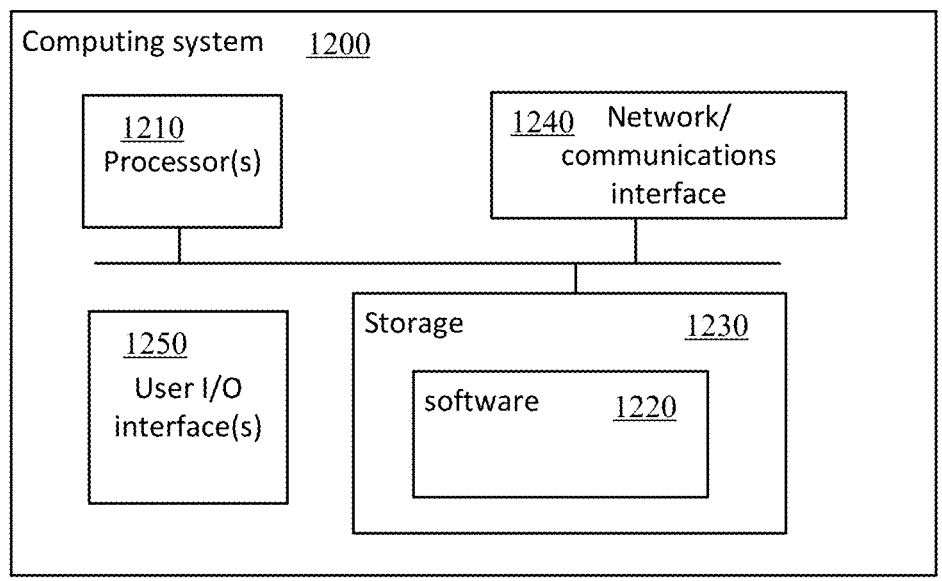
FIG. 12 illustrates components of a computing system that may be used in certain embodiments described herein.

FIG. 12 illustrates components of a computing system that may be used in certain embodiments described herein.

Referring to FIG. 12, system 1200 may be implemented within a single computing device or distributed across multiple computing devices or sub-systems that cooperate in executing program instructions. The system 1200 can include one or more blade server devices, standalone server devices, personal computers, laptops, tablets, mobile devices, routers, hubs, switches, bridges, firewall devices, intrusion detection devices, mainframe computers, network-attached storage devices, and other types of computing devices.

The system 1200 can include one or more processors 1210 that retrieves and executes software 1220 from storage 1230. Processing system 1210 may be implemented within a single processing device but may also be distributed across multiple processing devices or sub-systems that cooperate in executing program instructions.

Storage 1230 can include any computer readable storage media readable by processor(s) 1210 and capable of storing software 1220. Storage 1230 may be implemented as a single storage device but may also be implemented across multiple storage devices or sub-systems co-located or distributed relative to each other. Storage 1230 may include additional elements, such as a controller, capable of communicating with processor(s) 1210. Storage 1\2030 may also include storage devices and/or sub-systems on which data is stored. System 1200 may access one or more storage resources in order to access information to carry out any of the processes indicated by software 1220.

Software 1220 can include instructions and algorithms described with respect to the radiation prediction system and/or treatment plan system herein. For example, software 1220 can include neural network algorithms. In some cases, software 1220 includes instructions for the first CNN and the second CNN described with respect to FIG. 2 and the examples provided in Example 1. In some cases, software 1220 includes instructions for the projection generator and the cGAN (and CNN) described with respect to FIG. 3 and the example provided in Example 2. It should be understood that these examples are not intended to be limiting. Instructions for performing training of the various machine learning algorithms can also be included.

A communication interface 1240 may be included, providing communication connections and devices that allow for communication between system 1200 and other computing systems (not shown) over a communication network or collection of networks (not shown) or the air.

User input and output interfaces 1250 can also be included to enable input and output devices supporting human-machine interactions (e.g., keyboard, display, etc.).

In some embodiments, system 1200 may host one or more virtual machines.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules. As a non-limiting example, aspects of the neural networks and projection generator may be implemented in hardware modules such as available using FPGAs and ASICs.

It should be understood that as used herein, in no case do the terms "storage media," "computer-readable storage media" or "computer-readable storage medium" consist of transitory carrier waves or propagating signals. Instead, "storage" media refers to non-transitory media.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A radiation treatment planning system comprising:
    a machine learning system that receives patient data, a physician prescription of target dose, and device data and outputs predicted fluence maps, wherein the machine learning system comprises at least two stages, where a stage of the at least two stages includes converting image scans from the patient data to projection images; and
    a treatment planning system that receives the predicted fluence maps from the machine learning system and outputs a treatment plan.

2. The radiation treatment planning system of claim 1, wherein the machine learning system comprises at least one neural network selected from the group consisting of a DNN, a CNN, a GAN, and a cGAN.

3. The radiation treatment planning system of claim 1, wherein the machine learning system comprises:
    a first convolutional neural network (CNN) that receives the patient data and outputs predicted field-dose distributions; and a second CNN that receives beam's eye view (BEV) dose maps and outputs the predicted fluence maps, wherein the BEV dose maps are the projection images generated at an intermediate stage between the first CNN and the second CNN by projecting the predicted field-dose distributions onto BEV information received as part of the device data.

4. The radiation treatment planning system of claim 1, wherein the machine learning system comprises:
a projection generator that receives the patient data and the device data and generates the projection images; and
a convolutional neural network (CNN) that receives the projection images and outputs raw predicted fluence maps, the raw predicted fluence maps being post-processed to generate the predicted fluence maps.

5. The radiation treatment planning system of claim 4, wherein the CNN has a conditional Generative Adversarial Network (cGAN) architecture.

6. The radiation treatment planning system of claim 4, wherein the projection images comprise projections of each organ-at-risk at isocenter plane and projections of planning target volume (PTV)/clinical target volume (CTV) at both entrance and exit interfaces in a beam's eye view.

7. The radiation treatment planning system of claim 1, wherein the patient data comprises the image scans and contours.

8. The radiation treatment planning system of claim 1, wherein the machine learning system uses features comprising:
individual beam dose,
radiation characteristics to target volume or an organ-at-risk,
physician prescriptions of target dose,
organ dose tolerance, and
distance relationships among organs-at-risk and target volumes.

9. The radiation treatment planning system of claim 1, wherein converting image scans from the patient data to projection images uses the received physician prescription of target dose.

10. A method of automatic radiation treatment planning comprising:
receiving, at a machine learning system, patient data, a physician prescription of target dose, and device data;
converting, at the machine learning system, image scans from the patient data to projection images, wherein the machine learning system comprises at least two stages, where a stage of the at least two stages includes the converting of the image scans from the patient data to the projection images; and
outputting, from the machine learning system, predicted fluence maps.

11. The method of automatic radiation treatment planning of claim 10, further comprising:
receiving, at a treatment planning system, the predicted fluence maps;
performing, at the treatment planning system, leaf sequencing and final dose calculation; and
outputting, from the treatment planning system, a treatment plan based on the predicted fluence maps.

12. The method of automatic radiation treatment planning of claim 10, wherein the machine learning system comprises a first convolutional neural network (CNN) and a second CNN, the method further comprising:
generating, by the first CNN, predicted field-dose distributions from the received patient data; and
generating, by the second CNN, the predicted fluence maps.

13. The method of automatic radiation treatment planning of claim 12, wherein converting the image scans from the patient data to the projection images comprises:
projecting the predicted field-dose distributions generated by the first CNN onto beam's eye view (BEV) information received as part of the device data to generate BEV dose maps as the projection images, the BEV dose maps being input to the second CNN to generate the predicted fluence maps.

14. The method of automatic radiation treatment planning of claim 10, wherein the machine learning system comprises a convolutional neural network (CNN), the method further comprising:
generating, by the CNN, raw predicted fluence maps from the projection images; and
performing post-processing on the raw predicted fluence maps to generate the predicted fluence maps.

15. The method of automatic radiation treatment planning of claim 14, wherein performing the post-processing on the raw predicted fluence maps comprises:
performing Gaussian deconvolutions.

16. The method of automatic radiation treatment planning of claim 14, wherein converting the image scans from the patient data to the projection images comprises:
generating projections of each organ-at-risk at isocenter plane and projections of planning target volume (PTV)/clinical target volume (CTV) at both entrance and exit interfaces in a beam's eye view.

17. The method of automatic radiation treatment planning of claim 16, further comprising stacking the generated projections to form stacked images of the projection images, wherein the CNN receives the stacked images of the projection images to generate the raw predicted fluence maps.

18. The method of automatic radiation treatment planning of claim 10, wherein the machine learning system uses features comprising:
individual beam dose,
radiation characteristics to target volume or an organ-at-risk,
physician prescriptions of target dose,
organ dose tolerance, and
distance relationships among organs-at-risk and target volumes.

19. The method of automatic radiation treatment planning of claim 10, wherein converting image scans from the patient data to projection images uses the received physician prescription of target dose.

* * * * *